(12) United States Patent
Felle et al.

(10) Patent No.: US 10,676,728 B2
(45) Date of Patent: Jun. 9, 2020

(54) ENHANCED FERMENTATION

(71) Applicant: BASF SE, Ludwigshafen (DE)

(72) Inventors: Max Fabian Felle, Ludwigshafen (DE); Stefan Jenewein, Ludwigshafen (DE); Stefan Handtke, Greifswald (DE); Birgit Voigt, Greifswald (DE); Thomas Schweder, Greifswald (DE); Michael Hecker, Greifswald (DE)

(73) Assignee: BASF SE, Ludwigshafen (DE)

( * ) Notice: Subject to any disclaimer, the term of this patent is extended or adjusted under 35 U.S.C. 154(b) by 15 days.

(21) Appl. No.: 16/062,289

(22) PCT Filed: Dec. 8, 2016

(86) PCT No.: PCT/EP2016/080171
§ 371 (c)(1),
(2) Date: Jun. 14, 2018

(87) PCT Pub. No.: WO2017/102524
PCT Pub. Date: Jun. 22, 2017

(65) Prior Publication Data
US 2018/0371444 A1 Dec. 27, 2018

(30) Foreign Application Priority Data
Dec. 14, 2015 (EP) .................... 15199815

(51) Int. Cl.
| | |
|---|---|
| *C12N 9/54* | (2006.01) |
| *C12N 9/00* | (2006.01) |
| *C12N 9/64* | (2006.01) |
| *C12N 15/113* | (2010.01) |
| *C12N 15/52* | (2006.01) |
| *C12N 9/24* | (2006.01) |
| *C12N 9/08* | (2006.01) |
| *C12N 9/26* | (2006.01) |
| *C12N 9/42* | (2006.01) |

(52) U.S. Cl.
CPC ............ *C12N 9/54* (2013.01); *C12N 9/0065* (2013.01); *C12N 9/6408* (2013.01); *C12N 15/113* (2013.01); *C12N 15/52* (2013.01); *C12N 9/248* (2013.01); *C12N 9/2411* (2013.01); *C12N 9/2437* (2013.01); *C12N 9/2488* (2013.01); *C12Y 304/21062* (2013.01)

(58) Field of Classification Search
None
See application file for complete search history.

(56) References Cited

FOREIGN PATENT DOCUMENTS

WO WO-2010/074972 A1 7/2010

OTHER PUBLICATIONS

Sudhamsu et al., "Co-expression of ferrochelatase allows for complete heme incorporation into recombinant proteins produced in *E. coli*", Protein Expr Purif. Sep. 2010 ; 73(1): 78-82. doi:10.1016/j.pep.2010.03.010.*
"Bacillus pumilus SAFR-032, complete genome", NCBI Reference Sequence: NC_009848.4, 2 pp. (Apr. 5, 2017).
"*Bacillus subtilis* subsp. *subtilis* str. 168 chromosome, complete genome", NCBI Reference Sequence: NC_000964.3, 2 pp. (May 21, 2017).
"Structure of Bacillus pumilus catalase", PDB database under Accession No. 4QOL, 5 pp. (2015).
"Vegetative catalase 1—Bacillus subtilis subtilis 168", Accession IDs—BSU08820, P26901 (UniProt), 2 pp. (retrieved on Jul. 9, 2018).
Database UniProt [Online], "RecName: Full=Catalase{EC0:0000256:RuleBase:RU000498}; EC-1.11.1.6 { EC0:00002:5R6ul eBase:RU000498;}" XP002757020, retrieved from EBI accession No. UniProt:W6ANB4 (Apr. 16, 2014).
Database UniProt [Online], RecName: Full-Catalase{EC0:0000256:RuleBase:RU0004981; EC=I.11.1.6 { EC0:00002:5R6ul eBase:RU000498;}, XP002757019, retrieved from EBI accession No. UniProt: A8FBF9 (Nov. 13, 2007).
European Patent Application No. 15199815.0, Search Report, 5pp., dated May 9, 2016.
Gioia et al., Paradoxical DNA repair and peroxide resistance gene conservation in Bacillus pumilus SAFR-032, PLOS One, 2(9):e928 (Jan. 2007).
Handtke et al., Bacillus pumilus Reveals a Remarkably High Resistance to Hydrogen Peroxide Provoked Oxidative Stress, PLOS One, 9(1):e85625 (Jan. 2014).
Handtke et al., Cell physiology of the biotechnological relevant bacterium Bacillus pumilus—an omics-based approach, J. Biotechnol., 192 Pt A:204-14 (Dec. 2014).
International Patent Application No. PCT/EP2016/080171, International Search Report and Written Opinion, dated Mar. 6, 2017.
International Patent Application No. PCT/EP2016/080171, International Preliminary Report on Patentability, dated Jun. 19, 2018.
Loewen et al., Unprecedented access of phenolic substrates to the heme active site of a catalase: Substrate binding and peroxidase?like reactivity of Bacillus pumilus catalase monitored by X-ray crystallography and EPR spectroscopy, Proteins, 83(5):853-66 (2015).
Philibert et al., Heterologous expression and characterization of a new heme-catalase in Bacillus subtilis 168, J. Ind. Microbiol. Biotechnol., 43(6):729-40 (2016).
Sooch et al., Recent insights into microbial catalases: isolation, production and purification, Biotechnol. Adv., 32(8):1429-47 (2014).

\* cited by examiner

*Primary Examiner* — Suzanne M Noakes
(74) *Attorney, Agent, or Firm* — Marshall, Gerstein & Borun LLP

(57) ABSTRACT

The present invention generally relates to the field of fermentation technology and microorganisms useful for such fermentations. The invention also relates to materials including nucleic acids and proteins useful for altering fermentation characteristics of microorganisms, and to microorganisms comprising such nucleic acids and/or proteins. In particular, the invention relates to materials for conferring, modifying or reducing microbial stress resistance.

10 Claims, 5 Drawing Sheets

Specification includes a Sequence Listing.

SEQUENCE LISTING

<160> NUMBER OF SEQ ID NOS: 13

<210> SEQ ID NO 1
<211> LENGTH: 491
<212> TYPE: PRT
<213> ORGANISM: Bacillus pumilus

<400> SEQUENCE: 1

```
Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Thr
            20                  25                  30

Phe Leu Asp Asp Tyr His Leu Ile Glu Lys Leu Ala His Phe Asp Arg
        35                  40                  45

Glu Arg Ile Pro Glu Arg Val Val His Ala Arg Gly Ala Gly Ala Tyr
    50                  55                  60

Gly Val Phe Glu Val Glu Asn Ser Met Glu Lys His Thr Lys Ala Ala
65                  70                  75                  80

Phe Leu Ser Glu Glu Gly Lys Gln Thr Asp Val Phe Val Arg Phe Ser
                85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
    130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
                165                 170                 175

Met Leu Thr Trp Leu Phe Ser Asp Glu Gly Ile Pro Ala Asn Tyr Ala
            180                 185                 190

Glu Met Arg Gly Ser Gly Val His Thr Phe Arg Trp Val Asn Lys Tyr
        195                 200                 205

Gly Glu Thr Lys Tyr Val Lys Tyr His Trp Arg Pro Ser Glu Gly Ile
    210                 215                 220

Arg Asn Leu Ser Met Glu Glu Ala Ala Glu Ile Gln Ala Asn Asp Phe
225                 230                 235                 240

Gln His Ala Thr Arg Asp Leu Tyr Asp Arg Ile Glu Asn Gly Asn Tyr
                245                 250                 255

Pro Ala Trp Asp Leu Tyr Val Gln Leu Met Pro Leu Ser Asp Tyr Asp
            260                 265                 270

Asp Leu Asp Tyr Asp Pro Cys Asp Pro Thr Lys Thr Trp Ser Glu Glu
        275                 280                 285
```

```
Asp Tyr Pro Leu Gln Lys Val Gly Arg Met Thr Leu Asn Arg Asn Pro
    290                 295                 300

Glu Asn Phe Phe Ala Glu Thr Glu Gln Ser Ala Phe Thr Pro Ser Ala
305                 310                 315                 320

Leu Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
                340                 345                 350

Met Arg Ile Pro Val Asn Cys Pro Tyr Ala Pro Val His Asn Asn Gln
            355                 360                 365

Gln Asp Gly Phe Met Thr Thr Thr Arg Pro Ser Gly His Ile Asn Tyr
370                 375                 380

Glu Pro Asn Arg Tyr Asp Asp Gln Pro Lys Glu Asn Pro His Tyr Lys
385                 390                 395                 400

Glu Ser Glu Gln Val Leu His Gly Asp Arg Met Val Arg Gln Lys Ile
                405                 410                 415

Glu Lys Pro Asn Asp Phe Lys Gln Ala Gly Lys Tyr Arg Ser Tyr
                420                 425                 430

Ser Glu Glu Lys Gln Ala Leu Ile Lys Asn Leu Thr Ala Asp Leu
                435                 440                 445

Lys Asp Val Asn Asp Lys Thr Lys Leu Leu Ala Ile Cys Asn Phe Tyr
450                 455                 460

Arg Ala Asp Glu Asp Tyr Gly Gln Arg Leu Ala Asp Ser Leu Gly Val
465                 470                 475                 480

Asp Ile Arg Ser Tyr Leu Gln Gly Asn Met Lys
                485                 490

<210> SEQ ID NO 2
<211> LENGTH: 491
<212> TYPE: PRT
<213> ORGANISM: Bacillus pumilus

<400> SEQUENCE: 2

Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Thr
                20                  25                  30

Phe Leu Asp Asp Tyr His Leu Ile Glu Lys Leu Ala His Phe Asp Arg
            35                  40                  45

Glu Arg Ile Pro Glu Arg Val Val His Ala Arg Gly Ala Gly Ala Tyr
50                  55                  60

Gly Val Phe Glu Val Glu Asn Ser Met Glu Lys His Thr Lys Ala Ala
65                  70                  75                  80

Phe Leu Ser Glu Glu Gly Lys Gln Thr Asp Val Phe Val Arg Phe Ser
                85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
                165                 170                 175
```

```
Met Leu Thr Trp Leu Phe Ser Asp Glu Gly Ile Pro Ala Asn Tyr Ala
            180                 185                 190

Glu Met Arg Gly Ser Gly Val His Thr Phe Arg Trp Val Asn Lys Tyr
        195                 200                 205

Gly Glu Thr Lys Tyr Val Lys Tyr His Trp Arg Pro Ser Glu Gly Ile
        210                 215                 220

Arg Asn Leu Ser Met Glu Glu Ala Ala Glu Ile Gln Ala Asn Asp Phe
225                 230                 235                 240

Gln His Ala Thr Arg Asp Leu Tyr Asp Arg Ile Glu Asn Gly Asn Tyr
                245                 250                 255

Pro Ala Trp Asp Leu Tyr Val Gln Leu Met Pro Leu Ser Asp Tyr Asp
                260                 265                 270

Asp Leu Asp Tyr Asp Pro Cys Asp Pro Thr Lys Thr Trp Ser Glu Glu
            275                 280                 285

Asp Tyr Pro Leu Gln Lys Val Gly Arg Met Thr Leu Asn Arg Asn Pro
        290                 295                 300

Glu Asn Phe Phe Ala Glu Thr Glu Gln Val Ala Phe Thr Pro Ser Ala
305                 310                 315                 320

Leu Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
                340                 345                 350

Met Arg Ile Pro Val Asn Cys Pro Tyr Ala Pro Val His Asn Asn Gln
            355                 360                 365

Gln Asp Gly Phe Met Thr Thr Thr Arg Pro Ser Gly His Ile Asn Tyr
        370                 375                 380

Glu Pro Asn Arg Tyr Asp Asp Gln Pro Lys Glu Asn Pro His Tyr Lys
385                 390                 395                 400

Glu Ser Glu Gln Val Leu His Gly Asp Arg Met Val Arg Gln Lys Ile
                405                 410                 415

Glu Lys Pro Asn Asp Phe Lys Gln Ala Gly Glu Lys Tyr Arg Ser Tyr
            420                 425                 430

Ser Glu Glu Lys Gln Ala Leu Ile Lys Asn Leu Thr Ala Asp Leu
                435                 440                 445

Lys Asp Val Asn Asp Lys Thr Lys Leu Leu Ala Ile Cys Asn Phe Tyr
450                 455                 460

Arg Ala Asp Glu Asp Tyr Gly Gln Arg Leu Ala Asp Ser Leu Gly Val
465                 470                 475                 480

Asp Ile Arg Ser Tyr Leu Gln Gly Ser Met Lys
                485                 490

<210> SEQ ID NO 3
<211> LENGTH: 491
<212> TYPE: PRT
<213> ORGANISM: Bacillus pumilus

<400> SEQUENCE: 3

Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Thr
            20                  25                  30

Phe Leu Asp Asp Tyr His Leu Ile Glu Lys Leu Ala His Phe Asp Arg
        35                  40                  45

Glu Arg Ile Pro Glu Arg Val Val His Ala Arg Gly Ala Gly Ala Tyr
50                  55                  60
```

-continued

Gly Val Phe Glu Val Glu Asn Ser Met Glu Lys His Thr Lys Ala Ala
 65                  70                  75                  80

Phe Leu Ser Glu Asp Gly Lys Gln Thr Asp Val Phe Val Arg Phe Ser
             85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
            115                 120                 125

Gly Asn Asn Leu Pro Ile Phe Phe Ile Arg Asp Ala Leu Lys Phe Pro
        130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
                165                 170                 175

Met Leu Thr Trp Leu Phe Ser Asp Glu Gly Ile Pro Ala Asn Tyr Ala
                180                 185                 190

Glu Met Arg Gly Ser Gly Val His Thr Phe Arg Trp Val Asn Lys Tyr
            195                 200                 205

Gly Glu Thr Lys Tyr Val Lys Tyr His Trp Arg Pro Ser Glu Gly Ile
210                 215                 220

Arg Asn Leu Ser Met Glu Glu Ala Ala Glu Ile Gln Ala Asn Asp Phe
225                 230                 235                 240

Gln His Ala Thr Arg Asp Leu Tyr Asp Arg Ile Glu Asn Gly Asn Tyr
                245                 250                 255

Pro Ala Trp Asp Leu Tyr Val Gln Leu Met Pro Leu Ser Asp Tyr Asp
            260                 265                 270

Asp Leu Asp Tyr Asp Pro Cys Asp Pro Thr Lys Thr Trp Ser Glu Glu
            275                 280                 285

Asp Tyr Pro Leu Gln Lys Val Gly Arg Met Thr Leu Asn Arg Asn Pro
290                 295                 300

Glu Asn Phe Phe Ala Glu Thr Glu Gln Ser Ala Phe Thr Pro Ser Ala
305                 310                 315                 320

Leu Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
            340                 345                 350

Met Arg Ile Pro Val Asn Cys Pro Tyr Ala Pro Val His Asn Asn Gln
            355                 360                 365

Gln Asp Gly Phe Met Thr Thr Thr Arg Pro Ser Gly His Ile Asn Tyr
370                 375                 380

Glu Pro Asn Arg Tyr Asp Asp Gln Pro Lys Glu Asn Pro His Tyr Lys
385                 390                 395                 400

Glu Ser Glu Gln Val Leu His Asp Asp Arg Met Val Arg Gln Lys Ile
                405                 410                 415

Glu Lys Pro Asn Asp Phe Lys Gln Ala Gly Glu Lys Tyr Arg Ser Tyr
            420                 425                 430

Ser Glu Glu Glu Lys Gln Ala Leu Ile Lys Asn Leu Thr Ala Asp Leu
            435                 440                 445

Lys Asp Val Asn Asp Lys Thr Lys Leu Leu Ala Ile Cys Asn Phe Tyr
450                 455                 460

```
Arg Ala Asp Glu Asp Tyr Gly Gln Arg Leu Ala Asp Ser Leu Gly Val
465                 470                 475                 480

Asp Ile Arg Ser Tyr Leu Gln Gly Asn Met Lys
                485                 490

<210> SEQ ID NO 4
<211> LENGTH: 491
<212> TYPE: PRT
<213> ORGANISM: Bacillus pumilus

<400> SEQUENCE: 4

Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Thr
                20                  25                  30

Phe Leu Asp Asp Tyr His Leu Ile Glu Lys Leu Ala His Phe Asp Arg
            35                  40                  45

Glu Arg Ile Pro Glu Arg Val Val His Ala Arg Gly Ala Gly Ala Tyr
50                  55                  60

Gly Val Phe Glu Val Glu Asn Ser Met Glu Lys His Thr Lys Ala Ala
65                  70                  75                  80

Phe Leu Ser Glu Glu Gly Lys Gln Thr Asp Val Phe Val Arg Phe Ser
                85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
                165                 170                 175

Met Leu Thr Trp Leu Phe Ser Asp Glu Gly Ile Pro Ala Ser Tyr Ala
            180                 185                 190

Glu Met Arg Gly Ser Gly Val His Thr Phe Arg Trp Val Asn Lys Tyr
        195                 200                 205

Gly Glu Thr Lys Tyr Val Lys Tyr His Trp Arg Pro Ser Glu Gly Ile
210                 215                 220

Arg Asn Leu Ser Met Glu Glu Ala Ala Glu Ile Gln Ala Asn Asp Phe
225                 230                 235                 240

Gln His Ala Thr Arg Asp Leu Tyr Asp Arg Ile Glu Asn Gly His Tyr
                245                 250                 255

Pro Ala Trp Asp Leu Tyr Val Gln Leu Met Pro Leu Ser Asp Tyr Asp
            260                 265                 270

Asp Leu Asp Tyr Asp Pro Cys Asp Pro Thr Lys Thr Trp Ser Glu Glu
        275                 280                 285

Asp Tyr Pro Leu Gln Lys Val Gly Arg Met Thr Leu Asn Arg Asn Pro
290                 295                 300

Glu Asn Phe Phe Ala Glu Thr Glu Gln Ser Ala Phe Thr Pro Ser Ala
305                 310                 315                 320

Leu Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
            340                 345                 350
```

```
Met Arg Ile Pro Val Asn Cys Pro Tyr Ala Pro Val His Asn Asn Gln
            355                 360                 365

Gln Asp Gly Phe Met Thr Thr Thr Arg Pro Ser Gly His Ile Asn Tyr
        370                 375                 380

Glu Pro Asn Arg Tyr Asp Asp Gln Pro Lys Glu Asn Pro His Tyr Lys
385                 390                 395                 400

Glu Ser Glu Gln Val Leu His Gly Asp Arg Met Val Arg Gln Lys Ile
                405                 410                 415

Glu Lys Pro Asn Asp Phe Lys Gln Ala Gly Lys Tyr Arg Ser Tyr
            420                 425                 430

Ser Glu Glu Lys Gln Ala Leu Ile Lys Asn Leu Thr Ala Asp Leu
        435                 440                 445

Lys Asp Val Asn Asp Lys Thr Lys Leu Leu Ala Ile Cys Asn Phe Tyr
450                 455                 460

Arg Ala Asp Glu Asp Tyr Gly Gln Arg Leu Ala Asp Ser Leu Gly Val
465                 470                 475                 480

Asp Ile Arg Ser Tyr Leu Gln Gly Ser Met Lys
            485                 490
```

<210> SEQ ID NO 5
<211> LENGTH: 491
<212> TYPE: PRT
<213> ORGANISM: Bacillus pumilus

<400> SEQUENCE: 5

```
Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Ser
                20                  25                  30

Phe Leu Asp Asp Tyr His Leu Ile Glu Lys Leu Ala His Phe Asp Arg
            35                  40                  45

Glu Arg Ile Pro Glu Arg Val Val His Ala Arg Gly Ala Gly Ala Tyr
        50                  55                  60

Gly Val Phe Glu Val Glu Asn Ser Met Glu Lys His Thr Arg Ala Ala
65                  70                  75                  80

Phe Leu Ser Glu Lys Gly Lys Gln Thr Asp Val Phe Val Arg Phe Ser
                85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
            165                 170                 175

Met Leu Thr Trp Leu Phe Ser Asp Glu Gly Ile Pro Ala Asn Tyr Ala
        180                 185                 190

Glu Met Arg Gly Ser Gly Val His Thr Phe Arg Trp Val Asn Lys Tyr
    195                 200                 205

Gly Glu Thr Lys Tyr Val Lys Tyr His Trp Arg Pro Ser Glu Gly Ile
210                 215                 220

Arg Asn Leu Ser Met Glu Glu Ala Ala Glu Ile Gln Ala Asn Asp Phe
225                 230                 235                 240
```

Gln His Ala Thr Arg Asp Leu Tyr Asp Arg Ile Glu Lys Gly Asn Tyr
                245                 250                 255

Pro Ala Trp Asp Leu Tyr Val Gln Leu Met Pro Leu Ser Asp Tyr Asp
            260                 265                 270

Glu Leu Asp Tyr Asp Pro Cys Asp Pro Thr Lys Thr Trp Ser Glu Glu
        275                 280                 285

Asp Tyr Pro Leu Gln Lys Val Gly Arg Met Thr Leu Asn Arg Asn Pro
    290                 295                 300

Glu Asn Phe Phe Ala Glu Thr Glu Gln Ser Ala Phe Thr Pro Ser Ala
305                 310                 315                 320

Leu Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
            340                 345                 350

Met Arg Ile Pro Val Asn Cys Pro Tyr Ala Pro Val His Asn Asn Gln
        355                 360                 365

Gln Asp Gly Phe Met Thr Thr Thr Arg Pro Ser Gly His Ile Asn Tyr
    370                 375                 380

Glu Pro Asn Arg Tyr Asp Asp Gln Pro Lys Glu Asn Pro His Tyr Lys
385                 390                 395                 400

Glu Ser Glu Pro Val Leu His Gly Asp Arg Met Val Arg Gln Lys Ile
                405                 410                 415

Glu Lys Pro Asn Asp Phe Lys Gln Ala Gly Glu Arg Tyr Arg Ser Tyr
            420                 425                 430

Ser Glu Glu Glu Lys Gln Ala Leu Ile Lys Asn Leu Thr Ala Asp Leu
        435                 440                 445

Lys Asp Val Asn Asp Lys Thr Lys Leu Leu Ala Ile Cys Asn Phe Tyr
    450                 455                 460

Arg Ala Asp Glu Asp Tyr Gly Gln Arg Leu Ala Asp Ser Leu Gly Val
465                 470                 475                 480

Asp Ile Arg Ala Tyr Leu Gln Gly Asn Met Lys
                485                 490

<210> SEQ ID NO 6
<211> LENGTH: 491
<212> TYPE: PRT
<213> ORGANISM: Bacillus stratosphericus

<400> SEQUENCE:

```
Gly Phe Ala Val Lys Phe Tyr Thr Glu Glu Gly Asn Tyr Asp Leu Val
            115                 120                 125

Gly Asn Asn Leu Pro Ile Phe Ile Arg Asp Ala Leu Lys Phe Pro
        130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
                165                 170                 175

Met Leu Thr Trp Leu Phe Ser Asp Glu Gly Ile Pro Ala Asn Tyr Ala
                    180                 185                 190

Glu Met Arg Gly Ser Gly Val His Thr Phe Arg Trp Val Asn Lys Tyr
                195                 200                 205

Gly Glu Thr Lys Tyr Val Lys Tyr His Trp Arg Pro Ser Glu Gly Ile
    210                 215                 220

Arg Asn Leu Ser Met Glu Glu Ala Ala Glu Ile Gln Ala Asn Asp Phe
225                 230                 235                 240

Gln His Ala Thr Arg Asp Leu Tyr Asp Arg Ile Glu Lys Gly Asn Tyr
                245                 250                 255

Pro Ala Trp Asp Leu Tyr Val Gln Leu Met Pro Leu Ser Asp Tyr Asp
                260                 265                 270

Glu Leu Asp Tyr Asp Pro Cys Asp Pro Thr Lys Thr Trp Ser Glu Glu
            275                 280                 285

Asp Tyr Pro Leu Gln Lys Val Gly Arg Met Thr Leu Asn Arg Asn Pro
        290                 295                 300

Glu Asn Phe Phe Ala Glu Thr Glu Gln Ser Ala Phe Thr Pro Ser Ala
305                 310                 315                 320

Leu Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
                340                 345                 350

Met Arg Ile Pro Val Asn Cys Pro Tyr Ala Pro Val His Asn Asn Gln
            355                 360                 365

Gln Asp Gly Phe Met Thr Thr Thr Arg Pro Ser Gly His Ile Asn Tyr
        370                 375                 380

Glu Pro Asn Arg Tyr Asp Asp Gln Pro Lys Glu Asn Pro His Tyr Lys
385                 390                 395                 400

Glu Ser Glu Pro Val Leu His Gly Asp Arg Ile Val Arg Gln Lys Ile
                405                 410                 415

Glu Lys Pro Asn Asp Phe Lys Gln Ala Gly Glu Arg Tyr Arg Ser Tyr
                420                 425                 430

Ser Glu Glu Glu Lys Gln Ala Leu Ile Lys Asn Leu Thr Ala Asp Leu
            435                 440                 445

Lys Asp Val Asn Glu Lys Thr Lys Leu Leu Ala Ile Cys Asn Phe Tyr
450                 455                 460

Arg Ala Asp Glu Asp Tyr Gly Gln Arg Leu Ala Asp Ser Leu Gly Val
465                 470                 475                 480

Asp Ile Arg Ser Tyr Leu Gln Gly Ser Met Lys
                485                 490

<210> SEQ ID NO 7
<211> LENGTH: 491
<212> TYPE: PRT
<213> ORGANISM: Bacillus xiamenensis
```

<400> SEQUENCE: 7

Met Thr Asn Ser Asn His Lys His Leu Thr Thr Asn Gln Gly Val Pro
1               5                   10                  15

Val Gly Asp Asn Gln Asn Ser Arg Thr Ala Gly His Arg Gly Pro Ser
            20                  25                  30

Phe Leu Asp Asp Tyr His Leu Ile Glu Lys Leu Ala His Phe Asp Arg
        35                  40                  45

Glu Arg Ile Pro Glu Arg Val Val His Ala Arg Gly Ala Gly Ala Tyr
    50                  55                  60

Gly Val Phe Glu Val Glu Asn Ser Met Glu Lys His Thr Arg Ala Ala
65              70                  75                  80

Phe Leu Ser Glu Glu Gly Lys Gln Thr Asp Val Phe Val Arg Phe Ser
            85                  90                  95

Thr Val Ile His Pro Lys Gly Ser Pro Glu Thr Leu Arg Asp Pro Arg
        100                 105                 110

Gly Phe Ala Val Lys Phe Tyr Thr Glu Glu Gly Asn Tyr Asp Leu Val
    115                 120                 125

Gly Asn Asn Leu Pro Val Phe Phe Ile Arg Asp Ala Leu Lys Phe Pro
130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
            165                 170                 175

Met Leu Thr Trp Leu Phe Ser Asp Glu Gly Ile Pro Ala Asn Tyr Ala
        180                 185                 190

Glu Met Arg Gly Ser Gly Val His Thr Phe Arg Trp Val Asn Lys Tyr
    195                 200                 205

Gly Glu Thr Lys Tyr Val Lys Tyr His Trp Arg Pro Ser Glu Gly Ile
210                 215                 220

Arg Asn Leu Ser Met Glu Glu Ala Ala Glu Ile Gln Ala Asn Asp Phe
225                 230                 235                 240

Gln His Ala Thr Arg Asp Leu Tyr Asp Arg Ile Glu Lys Gly Asn Tyr
            245                 250                 255

Pro Ala Trp Asp Leu Tyr Val Gln Leu Met Pro Leu Ser Asp Tyr Asp
        260                 265                 270

Glu Leu Asp Tyr Asp Pro Cys Asp Pro Thr Lys Thr Trp Ser Glu Glu
    275                 280                 285

Asp Tyr Pro Leu Gln Lys Val Gly Arg Met Thr Leu Asn Arg Asn Pro
290                 295                 300

Glu Asn Phe Phe Ala Glu Thr Glu Gln Ser Ala Phe Thr Pro Ser Ala
305                 310                 315                 320

Leu Val Pro Gly Ile Glu Ala Ser Glu Asp Lys Leu Leu Gln Gly Arg
            325                 330                 335

Leu Phe Ser Tyr Pro Asp Thr Gln Arg His Arg Leu Gly Ala Asn Tyr
        340                 345                 350

Leu Arg Ile Pro Val Asn Cys Pro Tyr Ala Pro Val His Asn Asn Gln
    355                 360                 365

Gln Asp Gly Phe Met Thr Thr Thr Arg Pro Ser Gly His Ile Asn Tyr
370                 375                 380

Glu Pro Asn Arg Tyr Asp Asp Gln Pro Lys Glu Asn Pro His Tyr Lys
385                 390                 395                 400

Glu Ser Glu Pro Val Leu His Gly Asp Arg Met Val Arg Gln Lys Ile
            405                 410                 415

Glu Lys Pro Asn Asp Phe Lys Gln Ala Gly Glu Lys Tyr Arg Ser Tyr
            420                 425                 430

Ser Glu Glu Lys Gln Ala Leu Ile Lys Asn Leu Thr Ala Asp Leu
        435                 440                 445

Lys Asp Val Asn Glu Lys Thr Lys Leu Leu Ala Ile Cys Asn Phe Tyr
450                 455                 460

Arg Ala Asp Glu Asp Tyr Gly Gln Arg Leu Ala Asp Ser Leu Gly Val
465                 470                 475                 480

Asp Ile Arg Ser Tyr Leu Gln Gly Asn Met Lys
                485                 490

<210> SEQ ID NO 8
<211> LENGTH: 491
<212> TYPE: PRT
<213> ORGANISM: Bacillus pumilus

<400> SEQUENCE: 8

Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Ser
            20                  25                  30

Phe Leu Asp Asp Tyr His Leu Ile Glu Lys Leu Ala His Phe Asp Arg
        35                  40                  45

Glu Arg Ile Pro Glu Arg Val Val His Ala Arg Gly Ala Gly Ala Tyr
50                  55                  60

Gly Val Phe Glu Val Glu Asn Ser Met Glu Lys His Thr Arg Ala Ala
65                  70                  75                  80

Phe Leu Ser Glu Glu Gly Lys Gln Thr Asp Val Phe Val Arg Phe Ser
            85                  90                  95

Thr Val Ile His Pro Lys Gly Ser Pro Glu Thr Leu Arg Asp Pro Arg
        100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
                165                 170                 175

Met Leu Thr Trp Leu Phe Ser Asp Glu Gly Ile Pro Ala Asn Tyr Ala
        180                 185                 190

Glu Met Arg Gly Ser Gly Val His Thr Phe Arg Trp Val Asn Lys Tyr
        195                 200                 205

Gly Glu Thr Lys Tyr Val Lys Tyr His Trp Arg Pro Ser Glu Gly Ile
210                 215                 220

Arg Asn Leu Ser Met Glu Glu Ala Ala Glu Ile Gln Ala Asn Asp Phe
225                 230                 235                 240

Gln His Ala Thr Arg Asp Leu Tyr Asp Arg Ile Glu Lys Gly Asn Tyr
            245                 250                 255

Pro Ala Trp Asp Leu Tyr Val Gln Leu Met Pro Leu Ser Asp Tyr Asp
        260                 265                 270

Glu Leu Asp Tyr Asp Pro Cys Asp Pro Thr Lys Thr Trp Ser Glu Glu
        275                 280                 285

Asp Tyr Pro Leu Gln Lys Val Gly Arg Met Thr Leu Asn Arg Asn Pro
290                 295                 300

```
Glu Asn Phe Phe Ala Glu Thr Glu Gln Ala Ala Phe Thr Pro Ser Ala
305                 310                 315                 320

Leu Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
                340                 345                 350

Met Arg Ile Pro Val Asn Cys Pro Tyr Ala Pro Val His Asn Asn Gln
                355                 360                 365

Gln Asp Gly Phe Met Thr Thr Thr Arg Pro Ser Gly His Ile Asn Tyr
        370                 375                 380

Glu Pro Asn Arg Tyr Asp Asp Gln Pro Lys Glu Asn Pro His Tyr Lys
385                 390                 395                 400

Glu Ser Glu Pro Val Leu His Gly Asp Arg Met Val Arg Gln Lys Ile
                405                 410                 415

Glu Lys Pro Asn Asp Phe Lys Gln Ala Gly Glu Lys Tyr Arg Ser Tyr
                420                 425                 430

Ser Glu Glu Glu Lys Gln Ala Leu Ile Lys Asn Leu Thr Ala Asp Leu
                435                 440                 445

Lys Gly Val Asn Glu Lys Thr Lys Leu Leu Ala Ile Cys Asn Phe Tyr
450                 455                 460

Arg Ala Asp Glu Asp Tyr Gly Gln Arg Leu Ala Asp Ser Leu Gly Val
465                 470                 475                 480

Asp Ile Arg Ser Tyr Leu Gln Gly Ser Met Lys
                485                 490

<210> SEQ ID NO 9
<211> LENGTH: 491
<212> TYPE: PRT
<213> ORGANISM: Bacillus pumilus

<400> SEQUENCE: 9

Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Ser Ser
                20                  25                  30

Phe Leu Asp Asp Tyr His Leu Ile Glu Lys Leu Ala His Phe Asp Arg
            35                  40                  45

Glu Arg Ile Pro Glu Arg Val Val His Ala Arg Gly Ala Gly Ala Tyr
50                  55                  60

Gly Val Phe Glu Val Glu Asn Ser Met Glu Lys His Thr Arg Ala Ala
65                  70                  75                  80

Phe Leu Ser Glu Glu Gly Lys Gln Thr Asp Val Phe Val Arg Phe Ser
                85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
130                 135                 140

Asp Met Val His Ser Leu Lys Pro Asp Pro Val Ala Asn Ile Gln Asp
145                 150                 155                 160

Pro Asp Arg Tyr Trp Asp Phe Met Thr Leu Thr Pro Glu Ser Thr His
                165                 170                 175

Met Leu Thr Trp Leu Phe Ser Asp Glu Gly Ile Pro Ala Asn Tyr Ala
            180                 185                 190
```

```
Glu Met Arg Gly Ser Gly Val His Thr Phe Arg Trp Val Asn Lys Tyr
            195                 200                 205

Gly Glu Thr Lys Tyr Val Lys Tyr His Trp Arg Pro Ser Glu Gly Ile
210                 215                 220

Arg Asn Leu Ser Met Glu Ala Ala Glu Ile Gln Ala Asn Asp Phe
225                 230                 235                 240

Gln His Ala Thr Arg Asp Leu Tyr Asp Arg Ile Glu Lys Gly Asn Tyr
            245                 250                 255

Pro Ala Trp Asp Leu Tyr Val Gln Leu Met Pro Leu Ser Asp Tyr Asp
            260                 265                 270

Glu Leu Asp Tyr Asp Pro Cys Asp Pro Thr Lys Thr Trp Ser Glu Glu
            275                 280                 285

Asp Tyr Pro Leu Gln Lys Val Gly Arg Met Thr Leu Asn Arg Asn Pro
290                 295                 300

Glu Asn Phe Phe Ala Glu Thr Glu Gln Ser Ala Phe Thr Pro Ser Ala
305                 310                 315                 320

Leu Val Pro Gly Ile Glu Ala Ser Glu Asp Lys Leu Leu Gln Gly Arg
                325                 330                 335

Leu Phe Ser Tyr Pro Asp Thr Gln Arg His Arg Pro Gly Ala Asn Tyr
            340                 345                 350

Met Arg Ile Pro Val Asn Cys Pro Tyr Ala Pro Val His Asn Asn Gln
        355                 360                 365

Gln Asp Gly Phe Met Thr Thr Thr Arg Pro Ser Gly His Ile Asn Tyr
    370                 375                 380

Glu Pro Asn Arg Tyr Asp Asp Gln Pro Lys Glu Asn Pro His Tyr Lys
385                 390                 395                 400

Glu Ser Glu Pro Val Leu His Gly Asp Arg Met Val Arg Gln Lys Ile
                405                 410                 415

Glu Lys Pro Asn Asp Phe Lys Gln Ala Gly Glu Lys Tyr Arg Ser Tyr
            420                 425                 430

Ser Glu Glu Glu Lys Gln Ala Leu Ile Lys Asn Leu Thr Ala Asp Leu
        435                 440                 445

Lys Asp Val Asn Glu Lys Thr Lys Leu Leu Ala Ile Cys Asn Phe Tyr
450                 455                 460

Arg Ala Asp Glu Asp Tyr Gly Gln Arg Ser Ala Asp Ser Leu Gly Val
465                 470                 475                 480

Asp Ile Arg Ser Tyr Leu Gln Gly Asn Met Lys
                485                 490
```

<210> SEQ ID NO 10
<211> LENGTH: 491
<212> TYPE: PRT
<213> ORGANISM: Bacillus sp.

<400> SEQUENCE: 10

```
Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Thr
                20                  25                  30

Phe Leu Asp Asp Tyr His Leu Ile Glu Lys Leu Ala His Phe Asp Arg
            35                  40                  45

Glu Arg Ile Pro Glu Arg Val Val His Ala Arg Gly Ala Gly Ala Tyr
50                  55                  60

Gly Val Phe Glu Val Glu Asn Ser Met Glu Lys His Thr Lys Ala Ala
65                  70                  75                  80
```

```
Phe Leu Ser Glu Glu Gly Lys Gln Thr Asp Val Phe Val Arg Phe Ser
                 85                  90                  95
Thr Val Ile His Pro Lys Gly Ser Pro Glu Thr Leu Arg Asp Pro Arg
            100                 105                 110
Gly Phe Ala Val Lys Phe Tyr Thr Glu Glu Gly Asn Tyr Asp Leu Val
        115                 120                 125
Gly Asn Asn Leu Pro Ile Phe Phe Ile Arg Asp Ala Leu Lys Phe Pro
    130                 135                 140
Asp Met Val His Ser Leu Lys Pro Asp Pro Val Thr Asn Ile Gln Asp
145                 150                 155                 160
Pro Asp Arg Tyr Trp Asp Phe Met Thr Leu Thr Pro Glu Ser Thr His
                165                 170                 175
Met Leu Thr Trp Leu Phe Ser Asp Glu Gly Ile Pro Ala Ser Tyr Ala
            180                 185                 190
Glu Met Arg Gly Ser Gly Val His Thr Phe Arg Trp Val Asn Lys Tyr
        195                 200                 205
Gly Glu Ala Lys Tyr Val Lys Tyr His Trp Arg Pro Ser Glu Gly Ile
    210                 215                 220
His Asn Leu Ser Met Glu Glu Ala Ala Glu Ile Gln Ala Asn Asp Phe
225                 230                 235                 240
Gln His Ala Thr Arg Asp Leu Tyr Asp Arg Ile Glu Lys Gly Asn Phe
                245                 250                 255
Pro Ala Trp Asp Leu Tyr Val Gln Leu Met Pro Leu Ser Asp Tyr Asp
            260                 265                 270
Glu Leu Asp Tyr Asp Pro Cys Asp Pro Thr Lys Thr Trp Ser Glu Glu
        275                 280                 285
Asp Tyr Pro Leu Gln Lys Val Gly Arg Met Thr Leu Asn Arg Asn Pro
    290                 295                 300
Glu Asn Phe Phe Ala Glu Thr Glu Gln Ser Ala Phe Thr Pro Ser Ala
305                 310                 315                 320
Phe Val Pro Gly Ile Glu Ala Ser Glu Asp Lys Leu Leu Gln Gly Arg
                325                 330                 335
Leu Phe Ser Tyr Pro Asp Thr Gln Arg His Arg Leu Gly Ala Asn Tyr
            340                 345                 350
Met Arg Ile Pro Val Asn Cys Pro Tyr Ala Pro Val His Asn Asn Gln
        355                 360                 365
Gln Asp Gly Phe Met Thr Thr Thr Arg Pro Ser Gly His Ile Asn Tyr
    370                 375                 380
Glu Pro Asn Arg Tyr Asp Asp Gln Pro Lys Glu Asn Pro His Tyr Lys
385                 390                 395                 400
Glu Ser Glu Pro Val Leu His Gly Asp Arg Met Val Arg Gln Lys Ile
                405                 410                 415
Glu Lys Pro Asn Asp Phe Lys Gln Ala Gly Glu Arg Tyr Arg Ser Tyr
            420                 425                 430
Ser Glu Glu Glu Lys Gln Ala Leu Ile Lys Asn Leu Thr Ala Asp Leu
        435                 440                 445
Lys Asp Val Asn Asp Lys Thr Lys Leu Leu Ala Ile Cys Asn Phe Tyr
    450                 455                 460
Arg Ala Asp Glu Asp Tyr Gly Gln Arg Leu Ala Asp Ser Leu Gly Val
465                 470                 475                 480
Asp Ile Arg Ala Tyr Leu Gln Gly Ser Met Lys
                485                 490
```

<210> SEQ ID NO 11
<211> LENGTH: 491
<212> TYPE: PRT
<213> ORGANISM: Bacillus sp.

<400> SEQUENCE: 11

```
Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Thr
            20                  25                  30

Phe Leu Asp Asp Tyr His Leu Ile Glu Lys Leu Ala His Phe Asp Arg
        35                  40                  45

Glu Arg Ile Pro Glu Arg Val Val His Ala Arg Gly Ala Gly Ala Tyr
50                  55                  60

Gly Val Phe Glu Val Glu Asn Ser Met Glu Lys His Thr Lys Ala Ala
65                  70                  75                  80

Phe Leu Ser Glu Glu Gly Lys Gln Thr Asp Val Phe Val Arg Phe Ser
                85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
                165                 170                 175

Met Leu Thr Trp Leu Phe Ser Asp Glu Gly Ile Pro Ala Asn Tyr Ala
            180                 185                 190

Glu Met Arg Gly Ser Gly Val His Thr Phe Arg Trp Val Asn Lys Tyr
        195                 200                 205

Gly Glu Ala Lys Tyr Val Lys Tyr His Trp Arg Pro Ser Glu Gly Ile
210                 215                 220

Arg Asn Leu Ser Met Glu Glu Ala Ala Glu Ile Gln Ala Asn Asp Phe
225                 230                 235                 240

Gln His Ala Thr Arg Asp Leu Tyr Asp Arg Ile Glu Lys Gly Asn Phe
                245                 250                 255

Pro Ala Trp Asp Leu Tyr Val Gln Leu Met Pro Leu Ser Asp Tyr Asp
            260                 265                 270

Glu Leu Asp Tyr Asp Pro Cys Asp Pro Thr Lys Thr Trp Ser Glu Glu
        275                 280                 285

Asp Tyr Pro Leu Gln Lys Val Gly Arg Met Thr Leu Asn Arg Asn Pro
290                 295                 300

Asp Asn Phe Phe Ala Glu Thr Glu Gln Ser Ala Phe Thr Pro Ser Ala
305                 310                 315                 320

Phe Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
            340                 345                 350

Met Arg Ile Pro Val Asn Cys Pro Tyr Ala Pro Val His Asn Asn Gln
        355                 360                 365

Gln Asp Gly Phe Met Thr Thr Thr Arg Pro Ser Gly His Ile Asn Tyr
370                 375                 380
```

```
-continued

Glu Pro Asn Arg Tyr Ala Asp Gln Pro Lys Glu Asn Pro His Tyr Lys
385                 390                 395                 400

Glu Ser Glu Pro Val Leu His Gly Asp Arg Met Val Arg Gln Lys Ile
            405                 410                 415

Glu Lys Pro Asn Asp Phe Lys Gln Ala Gly Glu Lys Tyr Arg Ser Tyr
        420                 425                 430

Ser Glu Glu Glu Lys Gln Ala Leu Ile Lys Asn Leu Thr Ala Asp Leu
    435                 440                 445

Lys Asp Val Asn Asp Gln Thr Lys Leu Leu Ala Ile Cys Asn Phe Tyr
450                 455                 460

Arg Ala Asp Glu Asp Tyr Gly Gln Arg Leu Ala Asp Ser Leu Gly Val
465                 470                 475                 480

Asp Ile Arg Ala Tyr Leu Gln Gly Ser Met Lys
                485                 490

<210> SEQ ID NO 12
<211> LENGTH: 491
<212> TYPE: PRT
<213> ORGANISM: Bacillus sp.

<400> SEQUENCE: 12

Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Thr
            20                  25                  30

Phe Leu Asp Asp Tyr His Leu Ile Glu Lys Leu Ala His Phe Asp Arg
        35                  40                  45

Glu Arg Ile Pro Glu Arg Val Val His Ala Arg Gly Ala Gly Ala Tyr
50                  55                  60

Gly Val Phe Glu Val Glu Asn Ser Met Glu Lys His Thr Lys Ala Ala
65                  70                  75                  80

Phe Leu Ser Glu Glu Gly Lys Gln Thr Asp Val Phe Val Arg Phe Ser
                85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
130                 135                 140

Asp Met Val His Ser Leu Lys Pro Asp Pro Val Thr Asn Ile Gln Asp
145                 150                 155                 160

Pro Asp Arg Tyr Trp Asp Phe Met Thr Leu Thr Pro Glu Ser Thr His
                165                 170                 175

Met Leu Thr Trp Leu Phe Ser Asp Glu Gly Ile Pro Ala Ser Tyr Ala
            180                 185                 190

Glu Met Arg Gly Ser Gly Val His Thr Phe Arg Trp Val Asn Lys Tyr
        195                 200                 205

Gly Glu Ala Lys Tyr Val Lys Tyr His Trp Arg Pro Ser Glu Gly Ile
210                 215                 220

Arg Asn Leu Ser Met Glu Glu Ala Glu Ile Gln Ala Asn Asp Phe
225                 230                 235                 240

Gln His Ala Thr Arg Asp Leu Tyr Asp Arg Ile Glu Lys Gly Asn Phe
                245                 250                 255

Pro Ala Trp Asp Leu Tyr Val Gln Leu Met Pro Leu Ser Asp Tyr Asp
            260                 265                 270
```

-continued

```
Glu Leu Asp Tyr Asp Pro Cys Asp Pro Thr Lys Thr Trp Ser Glu Glu
            275                 280                 285

Asp Tyr Pro Leu Gln Lys Val Gly Arg Met Thr Leu Asn Arg Asn Pro
    290                 295                 300

Glu Asn Phe Phe Ala Glu Thr Glu Gln Ser Ala Phe Thr Pro Ser Ala
305                 310                 315                 320

Phe Val Pro Gly Ile Glu Ala Ser Glu Asp Lys Leu Leu Gln Gly Arg
                325                 330                 335

Leu Phe Ser Tyr Pro Asp Thr Gln Arg His Arg Leu Gly Ala Asn Tyr
            340                 345                 350

Met Arg Ile Pro Val Asn Cys Pro Tyr Ala Pro Val His Asn Asn Gln
        355                 360                 365

Gln Asp Gly Phe Met Thr Thr Thr Arg Pro Ser Gly His Ile Asn Tyr
    370                 375                 380

Glu Pro Asn Arg Tyr Ala Asp Gln Pro Lys Glu Asn Pro His Tyr Lys
385                 390                 395                 400

Glu Ser Glu Pro Val Leu His Gly Asp Arg Met Val Arg Gln Lys Ile
                405                 410                 415

Glu Lys Pro Asn Asp Phe Lys Gln Ala Gly Glu Lys Tyr Arg Ser Tyr
            420                 425                 430

Ser Glu Glu Glu Lys Gln Ala Leu Ile Lys Asn Leu Thr Ala Asp Leu
        435                 440                 445

Lys Asp Val Asn Asp Gln Thr Lys Leu Leu Ala Ile Cys Asn Phe Tyr
    450                 455                 460

Arg Ala Asp Glu Asp Tyr Gly Gln Arg Leu Ala Asp Ser Leu Gly Val
465                 470                 475                 480

Asp Ile Arg Ala Tyr Leu Gln Gly Ser Met Lys
                485                 490

<210> SEQ ID NO 13
<211> LENGTH: 491
<212> TYPE: PRT
<213> ORGANISM: Bacillus sp.

<400> SEQUENCE: 13

Met Thr Asn Ser Asn His Lys Asn Leu Thr Thr Asn Gln Gly Val Pro
1               5                   10                  15

Val Gly Asp Asn Gln Asn Ser Arg Thr Ala Gly His Arg Gly Pro Ser
            20                  25                  30

Phe Leu Asp Asp Tyr His Leu Ile Glu Lys Leu Ala His Phe Asp Arg
        35                  40                  45

Glu Arg Ile Pro Glu Arg Val Val His Ala Arg Gly Ala Gly Ala Tyr
    50                  55                  60

Gly Val Phe Glu Val Glu Asn Ser Met Glu Lys His Thr Arg Ala Ala
65                  70                  75                  80

Phe Leu Ser Glu Glu Gly Lys Gln Thr Asp Val Phe Val Arg Phe Ser
                85                  90                  95

Thr Val Ile His Pro Lys Gly Ser Pro Glu Thr Leu Arg Asp Pro Arg
            100                 105                 110

Gly Phe Ala Val Lys Phe Tyr Thr Glu Glu Gly Asn Tyr Asp Leu Val
        115                 120                 125

Gly Asn Asn Leu Pro Ile Phe Phe Ile Arg Asp Ala Leu Lys Phe Pro
    130                 135                 140

Asp Met Val His Ser Leu Lys Pro Asp Pro Val Thr Asn Ile Gln Asp
145                 150                 155                 160
```

-continued

```
Pro Asp Arg Tyr Trp Asp Phe Met Thr Leu Thr Pro Glu Ser Thr His
            165                 170                 175

Met Leu Thr Trp Leu Phe Ser Asp Glu Gly Ile Pro Ala Asn Phe Ala
            180                 185                 190

Glu Met Arg Gly Ser Gly Val His Thr Phe Arg Trp Val Asn Lys Tyr
            195                 200                 205

Gly Glu Thr Lys Tyr Val Lys Tyr His Trp Lys Pro Ser Glu Gly Ile
            210                 215                 220

Arg Asn Leu Ser Met Glu Ala Ala Glu Ile Gln Ala Asn Asp Phe
225                 230                 235                 240

Gln His Ala Thr Arg Asp Leu Phe Asp Arg Ile Glu Lys Gly Asn Tyr
            245                 250                 255

Pro Ala Trp Asp Leu Tyr Val Gln Leu Met Pro Leu Ser Asp Tyr Asp
            260                 265                 270

Glu Leu Asp Tyr Asp Pro Cys Asp Ser Thr Lys Thr Trp Ser Glu Glu
            275                 280                 285

Asp Tyr Pro Leu Gln Lys Val Gly Arg Met Thr Leu Asn Arg Asn Pro
            290                 295                 300

Glu Asn Phe Phe Ala Glu Thr Glu Gln Ser Ala Phe Thr Pro Ser Ala
305                 310                 315                 320

Leu Val Pro Gly Ile Glu Ala Ser Glu Asp Lys Leu Leu Gln Gly Arg
            325                 330                 335

Leu Phe Ser Tyr Pro Asp Thr Gln Arg His Arg Leu Gly Ala Asn Tyr
            340                 345                 350

Met Arg Ile Pro Val Asn Cys Pro Tyr Ala Pro Val His Asn Asn Gln
            355                 360                 365

Gln Asp Gly Phe Met Thr Thr Thr Arg Pro Ser Gly His Ile Asn Tyr
            370                 375                 380

Glu Pro Asn Arg Tyr Asp Asp Gln Pro Lys Glu Asn Pro His Tyr Lys
385                 390                 395                 400

Glu Ser Glu Pro Val Leu His Gly Asp Arg Met Val Arg Gln Lys Ile
            405                 410                 415

Glu Lys Pro Asn Asp Phe Lys Gln Ala Gly Glu Lys Tyr Arg Ser Tyr
            420                 425                 430

Ser Asp Glu Glu Lys Gln Ala Leu Ile Lys Asn Leu Thr Ala Asp Leu
            435                 440                 445

Lys Gly Val Asn Glu Lys Thr Lys Leu Leu Ala Ile Cys Asn Phe Tyr
            450                 455                 460

Arg Ala Asp Glu Asp Tyr Gly Gln Arg Leu Ala Asp Ser Leu Gly Val
465                 470                 475                 480

Asp Ile Arg Ser Tyr Leu Gln Gly Asn Met Lys
            485                 490
```

ENHANCED FERMENTATION

This application is a National Stage application of International Application No. PCT/EP2016/080171, filed Dec. 8, 2016, which claims the priority to European Patent Application No. 15199815.0, filed on Dec. 14, 2015.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "77568_Seqlisting.txt", which was created on Jun. 14, 2018 and is 55,503 bytes in size. The subject matter of the Sequence Listing is incorporated herein in its entirety by reference.

FIELD OF THE INVENTION

The present invention generally relates to the field of fermentation technology and microorganisms useful for such fermentations. The invention also relates to materials including nucleic acids and proteins useful for altering fermentation characteristics of microorganisms, and to microorganisms comprising such nucleic acids and/or proteins. In particular, the invention relates to materials for conferring, modifying or reducing microbial stress resistance against oxidative stress.

BACKGROUND OF THE INVENTION

The biotechnological production of substances of interest is, on an industrial scale, generally performed by cultivating a microorganism in a liquid medium, wherein said microorganism is capable of producing said substance of interest under the cultivation conditions. During such liquid fermentation, individual microorganism cells experience conditions that vary greatly and in a complex way over time. In response to such changing conditions, microorganism cells may respond by altering gene expression, which in turn may lead to an undesirably low production of the substance of interest. There is correspondingly a need to provide microorganisms with improved resilience against unfavourable fermentation conditions, thus allowing for an increased production of a substance of interest compared to comparable microorganisms.

It has thus frequently been tried to determine stress conditions during fermentations and to modify the genetic makeup of microorganisms in order to improve their resilience against such stress conditions. Unfortunately, analysis of fermentation conditions experienced by individual microorganism cells and their genetic reactions to such conditions is notoriously difficult. Wiegand et al. (Fermentation stage-dependent adaptations of *Bacillus licheniformis* during enzyme production; Microbial Cell Factories 2013, 12:120) have tried such analysis. However, understanding of fermentation conditions still remains largely incomplete.

While Wiegand et al. reported that no vegetative catalase (KatA) protein accumulation over time could be observed in *Bacillus licheniformis* during liquid fermentation production of a subtilisin protease, the inventors have surprisingly found that increased catalase activity improves overall fermentation characteristics e.g. of *B. licheniformis* in the liquid fermentation production of e.g. proteases. This was even more surprising as, according to Wiegand et al., O2 partial pressure (pO2) is severely reduced throughout basically all stages of such fermentation. Thus, formation of hydrogen peroxide as a major stressor was not to be expected.

It was thus an object of the present invention to provide materials and methods for improving fermentations, for reducing oxidative stress during fermentations, for removing hydrogen peroxide from a medium, for increasing hydrogen peroxide tolerance of a microorganism and/or for protecting a microbially produced substance against oxidation. It was also an object of the present invention to provide a suitable catalase for the aforementioned goals, and to provide microorganisms making use of such catalase, and to provide corresponding fermentation methods.

SUMMARY OF THE INVENTION

The present invention therefore provides a recombinant nucleic acid comprising a catalase gene coding for a polypeptide operably linked to one or more control sequences that direct the production of the polypeptide in an expression host, wherein the polypeptide is i) a catalase having at least 60% amino acid sequence identity to SEQ ID NO. 1, or ii) a fragment of the catalase according to i), wherein the fragment has catalase activity.

The present invention thus particularly provides a catalase including variants and fragments thereof. Accordingly, the present invention also provides nucleic acids, particularly recombinant nucleic acids, comprising a catalase gene coding for the catalase of the present invention to make this enzyme accessible for expression in microorganisms. The nucleic acid preferably is a construct or an expression vector.

The present invention also encompasses variants of the polypeptide of SEQ ID NO. 1 comprising a substitution, deletion, and/or insertion at one or more positions. Furthermore, the invention provides guidance for position specific and position non-specific replacements of amino acids from the amino acid sequence SEQ ID NO. 1.

The invention also provides a microorganism comprising, as a heterologous gene, a catalase gene coding for i) a catalase having at least 60% amino acid sequence identity to SEQ ID NO. 1, or ii) a fragment of the catalase according to i), wherein the fragment has catalase activity.

The gene thus refers to a catalase of the present invention including a variant or fragment thereof. The gene preferably is under the control of one or more control sequences that direct the production of the catalase of the present invention in a microorganism, optionally under predefined, limited conditions. The heterologous gene can be integrated into the genome of the microorganism and/or be present on a non-genomic nucleic acid, for example a plasmid.

The present invention also provides a method for producing a catalase, comprising the steps of a) providing a microorganism of the present invention, and b) cultivating the microorganism under conditions allowing for the expression of said gene.

As described herein, the gene preferably is operably linked to one or more control sequences that direct the production of the gene product, that is the catalase or fragment thereof. As also described herein, a control sequence is preferred which allows a hydrogen peroxide induced expression of said gene. By pre-treating the microorganism with a small dose of hydrogen peroxide, it is thus possible to selectively increase catalase production at a desired time during cultivation of said microorganism.

The invention also provides a method for removing hydrogen peroxide from a medium, comprising the steps of
a) providing a microorganism according to the present invention in said medium, and
b) cultivating the microorganism under conditions allowing for the expression of said gene.

Thus, the method envisages the cultivation of the microorganism under suitable conditions to produce a culture comprising the catalase of the present invention. Due to its catalase activity, the catalase of the present invention comprised in said culture will reduce the hydrogen peroxide comprised in the medium or provided by a microorganism present in said medium, possibly the microorganism of the present invention.

The invention also pertains to a method for increasing hydrogen peroxide tolerance of a microorganism, comprising
a) transforming a microorganism with a recombinant nucleic acid according to the invention, and
b) cultivating the microorganism under conditions allowing for the expression of said gene.

In those cases where the gene is operably linked to one or more control sequences that direct the production of the gene product, that is the catalase or fragment thereof, in a hydrogen peroxide dependent way, hydrogen peroxide tolerance of said microorganism can further be increased by exposing the microorganism being cultivated to a small dose of hydrogen peroxide. The dose of hydrogen peroxide is preferably adjusted to induce expression of the gene without significantly reducing the growth rate of said cultivated microorganism.

The invention also provides a method for protecting a microbially produced substance against oxidation, comprising
a) transforming a microorganism capable of producing said substance with a recombinant nucleic acid of the invention, or providing a microorganism according to the invention, and
b) cultivating the microorganism in said medium under conditions allowing for the expression of said catalase gene.

The catalase gene preferably is expressed before and/or during and/or after production of the microbially produced substance. Instead of the transformation in step a) the method of the present invention can also be performed by providing a correspondingly transformed microorganism or offspring thereof and cultivating the microorganism, as defined in step b). The microorganism may be the same microorganism which also produces the microbially produced substance to be protected against oxidation. The microorganism may also be added to one or more other microorganisms producing the microbially produced substance to be protected against oxidation.

The invention also provides a fermentation method for producing a fermentation product, comprising the steps of
a) transforming a microorganism capable of producing said substance with a recombinant nucleic acid comprising a catalase gene coding for a polypeptide according to the invention operably linked to one or more control sequences that direct the production of the polypeptide in an expression host, or providing a microorganism according to the invention, and
b) cultivating the microorganism under conditions allowing for the expression of said catalase gene and also allowing the production of said fermentation product.

The fermentation product may be produced by another microorganism co-cultivated with said microorganism of step a). It is also possible to have the microorganism of the present invention produce the fermentation product. As described herein, where the gene is operably linked to one or more control sequences that direct the production of the gene product, that is the catalase or fragment thereof, in the presence of hydrogen peroxide, it is preferred to expose the microorganism to a low dose of hydrogen peroxide sufficient for gene expression without significantly reducing the growth rate of the microorganism and/or without significantly reducing the production rate of said fermentation product.

These and other aspects of the invention will be further explained the following description.

DETAILED DESCRIPTION OF THE INVENTION

Figure 1:
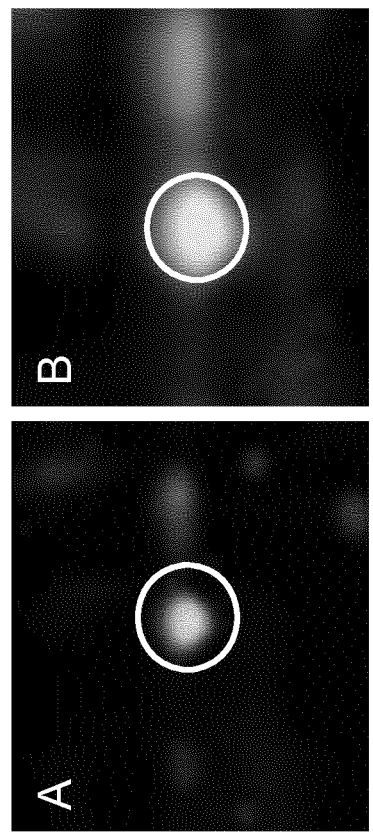
FIG. 1 shows a KatX2 protein spot in 2D gel electrophoresis of exponentially growing *B. pumilus* cells (A) and following treatment with 2 mM H2O2 (B). Protein accumulation is shown in green, reversible oxidized thiol-modifications stained with BODIPY fluorescent stain is shown in red.

The present invention is particularly concerned with catalases. In this regard, the invention puts particular emphasis on a catalase having the amino acid sequence of SEQ ID NO. 1, variants of such catalase and fragments thereof. Thus, the term "catalase of the present invention" refers to a polypeptide comprising or consisting of the amino acid sequence SEQ ID NO. 1, to variants of such polypeptide comprising or consisting of an amino acid sequence having at least 60% amino acid sequence identity to the sequence according to SEQ ID NO. 1, and also to fragments of such polypeptides, unless a different meaning is expressly attributed to the term. It is understood that the variants and fragments have catalase activity.

A catalase of the present invention is particularly known from *Bacillus pumilus* under the common name KatX2. The amino acid sequence of the catalase KatX2 of *Bacillus*

*pumilus* has been determined repeatedly and is recorded in the Uniprot database under accession numbers B4AFT4_BACPU, A8FBF9_BACP2, A0A063Z4T4_BACPU, A0A0B0QA43_9 BACI, M5RKX5_9 BACI, K2MHE7_9 BACI, W8QL66_BACPU, W6ANB4_BACPU, A0A0B4S5R6_9 BACI, A0A059NBL2_9 BACI, A0A0C2PYN3_BACPU and A0A081LAW9_9 BACI, as indicated therein on 8 Oct. 2015. According to the present invention, the catalase KatX2 preferably consists of or comprises the amino acid sequence according to SEQ ID NO. 1. However, any other catalase recorded under the aforementioned Uniprot identifiers (sequences SEQ ID NO. 2-13) is likewise considered a catalase of the present invention.

Thus, catalase sequences according to the present invention are in particular selected from:

| SEQ ID NO. | Uniprot idenfifier | sequence |
|---|---|---|
| 1 | KatX2-Bpu | MTNSNHKNLTTNQGVPVGDNQNSRTAGHRGPTFLDDYHLIEKL AHFDRERIPERVVHARGAGAYGVFEVENSMEKHTKAAFLSEEG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPANYAEMRGSGVHTFRVVVNKYGETKWKYH WRPSEGIRNLSMEEAAEIQANDFQHATRDLYDRIENGNYPAWD LYVQLMPLSDYDDLDYDPCDPTKTWSEEDYPLQKVGRMTLNRN PENFFAETEQSAFTPSALVPGIEASEDKLLQGRLFSYPDTQRHR LGANYMRIPVNCPYAPVHNNQQDGFMTTTRPSGHINYEPNRYD DQPKENPHYKESEQVLHGDRMVRQKIEKPNDFKQAGEKYRSY SEEEKQALIKNLTADLKDVNDKTKLLAICNFYRADEDYGQRLADS LGVDIRSYLQGNMK |
| 2 | B4AFT4_BACPU | MTNSNHKNLTTNQGVPVGDNQNSRTAGHRGPTFLDDYHLIEKL AHFDRERIPERVVHARGAGAYGVFEVENSMEKHTKAAFLSEEG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPANYAEMRGSGVHTFRVVVNKYGETKYVKYH WRPSEGIRNLSMEEAAEIQANDFQHATRDLYDRIENGNYPAWD LYVQLMPLSDYDDLDYDPCDPTKTWSEEDYPLQKVGRMTLNRN PENFFAETEQVAFTPSALVPGIEASEDKLLQGRLFSYPDTQRHR LGANYMRIPVNCPYAPVHNNQQDGFMTTTRPSGHINYEPNRYD DQPKENPHYKESEQVLHGDRMVRQKIEKPNDFKQAGEKYRSY SEEEKQALIKNLTADLKDVNDKTKLLAICNFYRADEDYGQRLADS LGVDIRSYLQGSMK |
| 3 | A8FBF9_BACP2 | MTNSNHKNLTTNQGVPVGDNQNSRTAGHRGPTFLDDYHLIEKL AHFDRERIPERVVHARGAGAYGVFEVENSMEKHTKAAFLSEDG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPANYAEMRGSGVHTFRVVVNKYGETKYVKYH WRPSEGIRNLSMEEAAEIQANDFQHATRDLYDRIENGNYPAWD LYVQLMPLSDYDDLDYDPCDPTKTWSEEDYPLQKVGRMTLNRN PENFFAETEQSAFTPSALVPGIEASEDKLLQGRLFSYPDTQRHR LGANYMRIPVNCPYAPVHNNQQDGFMTTTRPSGHINYEPNRYD DQPKENPHYKESEQVLHDDRMVRQKIEKPNDFKQAGEKYRSYS EEEKQALIKNLTADLKDVNDKTKLLAICNFYRADEDYGQRLADSL GVDIRSYLQGNMK |
| 4 | A0A063Z4T4_BACPU | MTNSNHKNLTTNQGVPVGDNQNSRTAGHRGPTFLDDYHLIEKL AHFDRERIPERVVHARGAGAYGVFEVENSMEKHTKAAFLSEEG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPASYAEMRGSGVHTFRVVVNKYGETKYVKYH WRPSEGIRNLSMEEAAEIQANDFQHATRDLYDRIENGHYPAWD LYVQLMPLSDYDDLDYDPCDPTKTWSEEDYPLQKVGRMTLNRN PENFFAETEQSAFTPSALVPGIEASEDKLLQGRLFSYPDTQRHR LGANYMRIPVNCPYAPVHNNQQDGFMTTTRPSGHINYEPNRYD DQPKENPHYKESEQVLHGDRMVRQKIEKPNDFKQAGEKYRSY SEEEKQALIKNLTADLKDVNDKTKLLAICNFYRADEDYGQRLADS LGVDIRSYLQGSMK |
| 5 | A0A0B0QA43_9BACI | MTNSNHKNLTTNQGVPVGDNQNSRTAGHRGPSFLDDYHLIEKL AHFDRERIPERVVHARGAGAYGVFEVENSMEKHTRAAFLSEKG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPANYAEMRGSGVHTFRVVVNKYGETKYVKYH WRPSEGIRNLSMEEAAEIQANDFQHATRDLYDRIEKGNYPAWD LYVQLMPLSDYDELDYDPCDPTKTWSEEDYPLQKVGRMTLNRN PENFFAETEQSAFTPSALVPGIEASEDKLLQGRLFSYPDTQRHR LGANYMRIPVNCPYAPVHNNQQDGFMTTTRPSGHINYEPNRYD DQPKENPHYKESEPVLHGDRMVRQKIEKPNDFKQAGERYRSYS EEEKQALIKNLTADLKDVNDKTKLLAICNFYRADEDYGQRLADSL GVDIRAYLQGNMK |

-continued

| SEQ ID NO. | Uniprot idenfifier | sequence |
|---|---|---|
| 6 | M5RKX5_9BACI | MTNSNHKNLTTNQGVPVGDNQNSRTAGHRGPSFLDDYHLIEKL AHFDRERIPERVVHARGAGAYGVFEVENSMEKHTRAAFLSEEG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPANYAEMRGSGVHTFRVVVNKYGETKYVKYH WRPSEGIRNLSMEEAAEIQANDFQHATRDLYDRIEKGNYPAWD LYVQLMPLSDYDELDYDPCDPTKTWSEEDYPLQKVGRMTLNRN PENFFAETEQSAFTPSALVPGIEASEDKLLQGRLFSYPDTQRHR LGANYMRIPVNCPYAPVHNNQQDGFMTTTRPSGHINYEPNRYD DQPKENPHYKESEPVLHGDRIVRQKIEKPNDFKQAGERYRSYS EEEKQALIKNLTADLKDVNEKTKLLAICNFYRADEDYGQRLADSL GVDIRSYLQGSMK |
| 7 | K2MHE7_9BACI | MTNSNHKHLTTNQGVPVGDNQNSRTAGHRGPSFLDDYHLIEKL AHFDRERIPERVVHARGAGAYGVFEVENSMEKHTRAAFLSEEG KQTDVFVRFSTVIHPKGSPETLRDPRGFAVKFYTEEGNYDLVGN NLPVFFIRDALKFPDMVHSLKPDPVTNIQDPDRYWDFMTLTPES THMLTWLFSDEGIPANYAEMRGSGVHTFRVVVNKYGETKYVKYH WRPSEGIRNLSMEEAAEIQANDFQHATRDLYDRIEKGNYPAWD LYVQLMPLSDYDELDYDPCDPTKTWSEEDYPLQKVGRMTLNRN PENFFAETEQSAFTPSALVPGIEASEDKLLQGRLFSYPDTQRHR LGANYLRIPVNCPYAPVHNNQQDGFMTTTRPSGHINYEPNRYD DQPKENPHYKESEPVLHGDRMVRQKIEKPNDFKQAGEKYRSYS EEEKQALIKNLTADLKDVNEKTKLLAICNFYRADEDYGQRLADSL GVDIRSYLQGNMK |
| 8 | W8QL66_BACPU | MTNSNHKNLTTNQGVPVGDNQNSRTAGHRGPSFLDDYHLIEKL AHFDRERIPERVVHARGAGAYGVFEVENSMEKHTRAAFLSEEG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPANYAEMRGSGVHTFRVVVNKYGETKYVKYH WRPSEGIRNLSMEEAAEIQANDFQHATRDLYDRIEKGNYPAWD LYVQLMPLSDYDELDYDPCDPTKTWSEEDYPLQKVGRMTLNRN PENFFAETEQAAFTPSALVPGIEASEDKLLQGRLFSYPDTQRHR LGANYMRIPVNCPYAPVHNNQQDGFMTTTRPSGHINYEPNRYD DQPKENPHYKESEPVLHGDRMVRQKIEKPNDFKQAGEKYRSYS EEEKQALIKNLTADLKGVNEKTKLLAICNFYRADEDYGQRLADSL GVDIRSYLQGSMK |
| 9 | W6ANB4_BACPU | MTNSNHKNLTTNQGVPVGDNQNSRTAGHRGSSFLDDYHLIEKL AHFDRERIPERVVHARGAGAYGVFEVENSMEKHTRAAFLSEEG KQTDVFVRFSTVIHPKGSPETLRDPRGFAVKFYTEEGNYDLVGN NLPIFFIRDALKFPDMVHSLKPDPVANIQDPDRYWDFMTLTPEST HMLTWLFSDEGIPANYAEMRGSGVHTFRWVNKYGETKYVKYH WRPSEGIRNLSMEEAAEIQANDFQHATRDLYDRIEKGNYPAWD LYVQLMPLSDYDELDYDPCDPTKTWSEEDYPLQKVGRMTLNRN PENFFAETEQSAFTPSALVPGIEASEDKLLQGRLFSYPDTQRHR PGANYMRIPVNCPYAPVHNNQQDGFMTTTRPSGHINYEPNRYD DQPKENPHYKESEPVLHGDRMVRQKIEKPNDFKQAGEKYRSYS EEEKQALIKNLTADLKDVNEKTKLLAICNFYRADEDYGQRSADSL GVDIRSYLQGNMK |
| 10 | A0A0B4S5R6_ 9BACI | MTNSNHKNLTTNQGVPVGDNQNSRTAGHRGPTFLDDYHLIEKL AHFDRERIPERVVHARGAGAYGVFEVENSMEKHTKAAFLSEEG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPASYAEMRGSGVHTFRVVVNKYGEAKYVKYH WRPSEGIHNLSMEEAAEIQANDFQHATRDLYDRIEKGNFPAWDL YVQLMPLSDYDELDYDPCDPTKTWSEEDYPLQKVGRMTLNRN PENFFAETEQSAFTPSAFVPGIEASEDKLLQGRLFSYPDTQRHR LGANYMRIPVNCPYAPVHNNQQDGFMTTTRPSGHINYEPNRYD DQPKENPHYKESEPVLHGDRMVRQKIEKPNDFKQAGERYRSYS EEEKQALIKNLTADLKDVNDKTKLLAICNFYRADEDYGQRLADSL GVDIRAYLQGSMK |
| 11 | A0A059NBL2_ 9BACI | MTNSNHKNLTTNQGVPVGDNQNSRTAGHRGPTFLDDYHLIEKL AHFDRERIPERVVHARGAGAYGVFEVENSMEKHTKAAFLSEEG KQTDVFVRFSTVIHPKGSPETLRDPRGFAVKFYTEEGNYDLVGN NLPIFFIRDALKFPDMVHSLKPDPVTNIQDPDRYWDFMTLTPEST HMLTWLFSDEGIPANYAEMRGSGVHTFRVVVNKYGEAKYVKYH WRPSEGIRNLSMEEAAEIQANDFQHATRDLYDRIEKGNFPAWDL YVQLMPLSDYDELDYDPCDPTKTWSEEDYPLQKVGRMTLNRN PDNFFAETEQSAFTPSAFVPGIEASEDKLLQGRLFSYPDTQRHR LGANYMRIPVNCPYAPVHNNQQDGFMTTTRPSGHINYEPNRYA |

-continued

| SEQ ID NO. | Uniprot idenfifier | sequence |
|---|---|---|
|  |  | DQPKENPHYKESEPVLHGDRMVRQKIEKPNDFKQAGEKYRSYS<br>EEEKQALIKNLTADLKDVNDQTKLLAICNFYRADEDYGQRLADSL<br>GVDIRAYLQGSMK |
| 12 | A0A0C2PYN3_<br>BACPU | MTNSNHKNLTTNQGVPVGDNQNSRTAGHRGPTFLDDYHLIEKL<br>AHFDRERIPERVVHARGAGAYGVFEVENSMEKHTKAAFLSEEG<br>KQTDVFVRFSTVIHPKGSPETLRDPRGFAVKFYTEEGNYDLVGN<br>NLPIFFIRDALKFPDMVHSLKPDPVTNIQDPDRYWDFMTLTPEST<br>HMLTWLFSDEGIPASYAEMRGSGVHTFRVVVNKYGEAKYVKYH<br>WRPSEGIRNLSMEEAAEIQANDFQHATRDLYDRIEKGNFPAWDL<br>YVQLMPLSDYDELDYDPCDPTKTWSEEDYPLQKVGRMTLNRN<br>PENFFAETEQSAFTPSAFVPGIEASEDKLLQGRLFSYPDTQRHR<br>LGANYMRIPVNCPYAPVHNNQQDGFMTTTRPSGHINYEPNRYA<br>DQPKENPHYKESEPVLHGDRMVRQKIEKPNDFKQAGEKYRSYS<br>EEEKQALIKNLTADLKDVNDQTKLLAICNFYRADEDYGQRLADSL<br>GVDIRAYLQGSMK |
| 13 | A0A081LAW9_<br>9BACI | MTNSNHKNLTTNQGVPVGDNQNSRTAGHRGPSFLDDYHLIEKL<br>AHFDRERIPERVVHARGAGAYGVFEVENSMEKHTRAAFLSEEG<br>KQTDVFVRFSTVIHPKGSPETLRDPRGFAVKFYTEEGNYDLVGN<br>NLPIFFIRDALKFPDMVHSLKPDPVTNIQDPDRYWDFMTLTPEST<br>HMLTWLFSDEGIPANFAEMRGSGVHTFRVVVNKYGETKYVKYH<br>WKPSEGIRNLSMEEAAEIQANDFQHATRDLFDRIEKGNYPAWDL<br>YVQLMPLSDYDELDYDPCDSTKTWSEEDYPLQKVGRMTLNRN<br>PENFFAETEQSAFTPSALVPGIEASEDKLLQGRLFSYPDTQRHR<br>LGANYMRIPVNCPYAPVHNNQQDGFMTTTRPSGHINYEPNRYD<br>DQPKENPHYKESEPVLHGDRMVRQKIEKPNDFKQAGEKYRSYS<br>DEEKQALIKNLTADLKGVNEKTKLLAICNFYRADEDYGQRLADSL<br>GVDIRSYLQGNMK |

*Bacillus pumilus* had been described as having a high resistance to hydrogen peroxide provoked oxidative stress (Handtke et al., "*Bacillus pumilus* Reveals a Remarkably High Resistance to Hydrogen Peroxide Provoked Oxidative Stress", PLOS ONE, January 2014, volume 9, pages 1 to 14). The authors of said publication describe that *Bacillus pumilus* is devoid of an otherwise common catalase KatA, which is involved in hydrogen peroxide defence of *Bacillus pumilus* and *Bacillus licheniformis*. In these bacilli, catalase KatA expression is induced by more than 100 fold upon exposition to hydrogen peroxide. In *Bacillus pumilus*, expression of KatX2 upon exposure to hydrogen peroxide is induced only up to 20 fold. The authors further note that upon exposure to hydrogen peroxide *Bacillus pumilus* induces a number of regulons, leading inter alia to an increased concentration of thiol compounds. Such compounds like bacillithiol have been known to protect intracellular substances against oxidation, for example by preventing reversible or irreversible cysteine oxidation. The authors also notice that a considerable set of hydrogen peroxide induced unique proteins with so far unknown function had been identified. Notably said publication has been subject of an expression of concern by the journal's editors (PLOS ONE, July 2014, Vol 9 Issue 7) on the grounds that the experiments described therein could not be repeated.

In another publication (Handtke et al., "Cell physiology of the biotechnological relevant bacterium *Bacillus pumilus*—an omics-based approach", Journal of Biotechnology 192 (2014), 204-214) the authors analysed changes in protein concentration of *Bacillus pumilus* during a model fermentation. The authors did not report any significant amount of KatX2 catalase in the total set of cytosolic proteins. It came thus as a surprise that KatX2 not only is a catalase having a particularly high catalytic activity, but also that KatX2 would improve fermentations production of other substances.

The present invention thus provides a nucleic acid comprising a catalase gene coding for a polypeptide operably linked to one or more control sequences that direct the production of the polypeptide in an expression host, wherein the polypeptide is i) a catalase having at least 60% amino acid sequence identity to SEQ ID NO. 1, or ii) a fragment of the catalase according to i), wherein the fragment has catalase activity.

Such recombinant nucleic acid particularly facilitates the expression of the catalase polypeptide as a heterologous gene in a microorganism, as described herein in more detail. Thus, the recombinant nucleic acid of the present invention allows to confer the benefits of expression of the catalase of the present invention not only in *Bacillus pumilus*, but also in other microorganisms.

According to the present invention, the term catalase and polypeptide having catalase activity are used interchangeably. Catalase activity can be determined as described in the examples section hereinafter by exposing a protein extract of a microorganism producing a polypeptide of putative catalase activity to hydrogen peroxide, incubating the extract and measuring remaining hydrogen peroxide concentration at defined time points.

The gene codes for a catalase having at least 60% amino acid sequence identity to SEQ ID NO. 1. Thus, the invention also encompasses variants of the mature polypeptide of SEQ ID NO. 1 comprising a substitution, deletion and/or insertion at one or more positions of the amino acid sequence SEQ ID NO. 1, and correspondingly also encompasses corresponding genes et cetera. As indicated above, all such catalase variants must have catalase activity.

The structure of KatX2 catalase is has been elucidated and is recorded in the PDB database under accession number 4QOL (DOI 10.2210/PDB4QOL/PDB). Variants of the catalase according to SEQ ID NO. 1 had been published under the aforementioned Uniprot identifiers and are repeated herein as sequences SEQ ID NO. 2-13. Thus, the skilled person is able to rationally construct new variants of the catalase according to SEQ ID NO. 1, keeping in mind that any substitution, deletion and/or insertion of one or more amino acids relative to the amino acid sequence of SEQ ID NO. 1 should not interfere with the three-dimensional folding of the amino acid chain, and should also not interfere with its agglomeration into a tetramer.

For providing new variants of the catalase according to amino acid sequence SEQ ID NO. 1, the skilled person can perform a pairwise alignment of the amino acid sequence SEQ ID NO. 1 with the amino acid sequence of another functional catalase. This way the skilled person can determine for each position of the amino acid sequence SEQ ID NO. 1 another amino acid found at the corresponding position of another catalase amino acid sequence known to have catalase activity. The skilled person can then replace, at each desired position, the amino acid encountered in the sequence according to SEQ ID NO. 1 by the corresponding amino acid found at the corresponding position of the other catalase. The same applies to insertions and deletions relative to the amino acid sequence according to SEQ ID NO. 1.

For substituting amino acids without regard to the occurrence of amino acid in other catalases, the following applies, wherein bracketed numbers indicate preference of replacement (higher numbers indicate higher preference): A may be replaced by any amino acid selected from S (1), C (0), G (0), T (0) or V (0). C may be replaced by A (0). D may be replaced by any amino acid selected from E (2), N (1), Q (0) or S (0). E may be replaced by any amino acid selected from D (2), Q (2), K (1), H (0), N (0), R (0) or S (0). F may be replaced by any amino acid selected from Y (3), W (1), I (0), L (0) or M (0). G may be replaced by any amino acid selected from A (0), N (0) or S (0). H may be replaced by any amino acid selected from Y (2), N (1), E (0), Q (0) or R (0). I may be replaced by any amino acid selected from V (3), L (2), M (1) or F (0). K may be replaced by any amino acid selected from R (2), E (1), Q (1), N (0) or S (0). L may be replaced by any amino acid selected from I (2), M (2), V (1) or F (0). M may be replaced by any amino acid selected from L (2), I (1), V (1), F (0) or Q (0). N may be replaced by any amino acid selected from D (1), H (1), S (1), E (0), G (0), K (0), Q (0), R (0) or T (0). Q may be replaced by any amino acid selected from E (2), K (1), R (1), D (0), H (0), M (0), N (0) or S (0). R may be replaced by any amino acid selected from K (2), Q (1), E (0), H (0) or N (0). S may be replaced by any amino acid selected from A (1), N (1), T (1), D (0), E (0), G (0), K (0) or Q (0). T may be replaced by any amino acid selected from S (1), A (0), N (0) or V (0). V may be replaced by any amino acid selected from I (3), L (1), M (1), A (0) or T (0). W may be replaced by any amino acid selected from Y (2) or F (1). Y may be replaced by any amino acid selected from F (3), H (2) or W (2).

Preferably, the variant of the polypeptide of SEQ ID NO. 1 has a higher sequence identity to SEQ ID NO. 1 than to the amino acid sequence of a KatA and/or KatX catalase of *Bacillus licheniformis* and/or *Bacillus subtilis*.

This way, when providing variants of the catalase according to SEQ ID NO. 1 the skilled person can avoid modifying the amino acid sequence according to SEQ ID NO. 1 in such way as to decrease catalytic activity of the variant catalase compared to the catalase according to SEQ ID NO. 1.

The catalase of the present invention preferably has at least 60% amino acid sequence identity to SEQ ID NO. 1. Even more preferably, the catalase has at least 70% amino acid sequence identity to SEQ ID NO. 1, even preferably at least 80% amino acid sequence identity to SEQ ID NO. 1, even more preferably at least 90% amino acid sequence identity to SEQ ID NO. 1, and even more preferably at least 95% amino acid sequence identity to SEQ ID NO. 1. With increasing sequence identity to SEQ ID NO. 1, the likelihood of a variant polypeptide having greatly reduced catalase activity is decreased. Correspondingly, the catalase preferably consists of an amino acid sequence differing from SEQ ID NO. 1 by not more than 15 substitutions, deletions and/or insertions of individual amino acids, even more preferably at most 14, more preferably by at most 13, more preferably by at most 12, more preferably by at most 11, more preferably by at most 10, more preferably by at most 9, more preferably by at most 8, more preferably by at most 7, more preferably by at most 6, more preferably by at most 5, more preferably by at most 4, more preferably by at most 3, more preferably by at most 2, most preferably by at most 1 substitutions, deletions and/or insertions of individual amino acids.

In a variant according to the present invention it is preferred not to delete or substitute cysteine moieties at positions 279 and/or 359 according to SEQ ID NO. 1. As described herein, upon exposure of the catalase according to SEQ ID NO. 1 to hydrogen peroxide only the thiol group of cysteine 461 is found to be modified by the formation of sulfonic acid at that position. The cysteine moieties at positions 279 and 359, however, seem to remain unaffected and thus might not require substitution or deletion.

According to the present invention, the catalase polypeptide can consist of an amino acid sequence as described above or a variant thereof having the required amino acid sequence identity. However, the present invention also provides for fragments of such catalase polypeptides, wherein the fragment has catalase activity. Such fragments may differ from the aforementioned amino acid sequences and variants thereof by the deletion of one or more amino acids at either end of the amino acid chain. Due to the requirement of maintaining the three-dimensional structure of the catalase to preserve its catalase activity, fragments according to the present invention differ from the aforementioned amino acid sequences or variants thereof preferably by not more than five amino acid deletions at either end of the amino acid chain, more preferably by at most for deletions, even more preferably by at most three deletions, even more preferably by at most two deletions, even more preferably by at most one deletion at either end of the amino acid chain. Fragments according to the invention allow for the production of polypeptides having catalase activity while reducing the amount of resources to produce such catalases. This is particularly advantageous under oxidative stress conditions like exposure to a hydrogen peroxide or internal production of hydrogen peroxide by a microorganism, as the microorganism under these conditions requires all of its resources for defence against said oxidative stress.

The recombinant nucleic acid according to the present invention comprises one or more control sequences that direct the production of the polypeptide in an expression host. The control sequence preferably comprises or is an inducible promoter, most preferably a hydrogen peroxide inducible promoter. Hydrogen peroxide induction can be determined by comparing, via Northern analysis or quantitative PCR, mRNA presence or concentration of a gene operably linked to said promoter in the presence or absence of H2O2. Preferably, a hydrogen peroxide inducible promoter results in an increase of said mRNA concentration by a factor of at least 4, even more preferably by a factor of at least 8, even more preferably by a factor of at least 10, even more preferably by a factor of at least 30, even more preferably by a factor of at least 90. Such promoters provide for the transcription of the gene under conditions where catalase activity actually is required, thereby making efficient use of the microorganism's resources. This way, the recombinant nucleic acid according to the present invention further facilitates fermentations by not unnecessarily redirecting resources that could be used for the firm entities production of a substance of interest as described herein. Preferred promotors are recorded under EMBL accession numbers. Preferred promoters are, for example, *Bacillus subtilis* KatA promoter and *Bacillus pumilus* KatX2 promoter, details of which can be found for example at bsubcyc.org/gene?orgid=BSUB&id=BSU08820 and under the Genbank identifiers NC_000964.3 and NC_009848.1, respectively.

Preferably, the one or more control sequences allow for the low basal expression of the gene. This way, the recombinant nucleic acid of the present invention allows an expression host to react immediately to the slow change in hydrogen peroxide concentrations, as occurs in fermentations.

The recombinant nucleic acid according to the present invention preferably is a nucleic acid construct or expression vector. This way, the recombinant nucleic acid allows to efficiently transform a microorganism into an expression host for expressing, preferably on demand as described above, the catalase of the present invention (which may be a variant or fragment as described above).

The invention also provides a microorganism comprising, as a heterologous gene, a catalase gene coding for
i) a catalase having at least 60% amino acid sequence identity to SEQ ID NO. 1, or
ii) a fragment of the catalase according to i), wherein the fragment has catalase activity.

The microorganism of the present invention is thus a recombinant microorganism. The microorganism may be obtained, as described herein, by transforming a wild type microorganism with the recombinant nucleic acid of the present invention. Thus, a microorganism according to the present invention can also be called a microorganism transformed with a catalase gene coding for said polypeptide. This definition excludes cells which were unsuccessfully transformed or which have lost the gene after the transformation event.

The microorganism may comprise the catalase gene in its genome or on a plasmid. Genomic integration of the gene can be achieved by any suitable means known to the skilled person and potentially chosen in view of the respective microorganism. Instructions for performing genomic integration can be found, for example, in Wach, A. (1996) PCR-synthesis of marker cassettes with long flanking homology regions for gene disruptions in *S. cerevisiae*. Yeast 12, 259-265, the contents of which are incorporated herein in their entirety. Genomic integration has the advantage that the gene coding for the catalase according to the present invention can be maintained during cultivation and fermentation even in the absence of selection pressure, e.g. antibiotic pressure. Also, genomic integration allows to have a native catalase gene of the microorganism replaced by the catalase gene of the present invention.

The microorganism can also comprise the gene on one or more plasmids. Such plasmids should be expression vectors according to the present invention, thereby leading to the expression of the gene coding for the catalase of the present invention under appropriate conditions according to the one or more control sequences. Generally, transformation of a microorganism with a plasmid is easier to achieve than genomic integration of the catalase gene. Microorganisms comprising such one or more plasmids are thus particularly preferred for producing variant catalases of the present invention to test their catalase activity.

It is understood that the microorganism according to the present invention comprises said gene operably linked to one or more control sequences that direct the production of the gene product, that is the catalase of fragment thereof. This allows to materialise the benefits indicated above in view of control sequences.

The microorganism can comprise the heterologous gene under the control of one or more heterologous control sequences. For example, the catalase promoter may be used as control sequence taken from a microorganism (source microorganism) closely related to the microorganism of the present invention (target microorganism). The source microorganism preferably is of the same class as the target microorganism, even more preferably of the same family as the target microorganism, even more preferably of the same genus as the target microorganism, and most preferably of the same species as the target microorganism. The closer the source and target microorganisms are phylogenetically related to each other, the more likely is it that the control sequence taken from a source microorganism directs the production of the corresponding catalase polypeptide in the target microorganism (expression host) under the same conditions as in the source microorganism.

The microorganism can be a prokaryote or a eukaryote. Preferably, the microorganism is a bacteria, an archaea, a fungal cell, a yeast cell or a eukaryotic cell.

Preferably, the microorganism of the present invention preferably belongs to the phylum Firmicutes or Proteobacteria. Preferably, the microorganism belongs to class Bacilli, to order Bacillales or Lactobacillales, to class Clostridia, to order Clostridiales, Halanaerobiales, Natranaerobiales, Thermoanaerobacterales, to class Erysipelotrichia, to order Erysipelotrichales, to class Limnochordia, to order Limnochordales, to class Negativicutes, to order Selenomonadales, to class Thermolithobacteria, to order Thermolithobacterales, to class Alphaproteobacteria, to order Caulobacterales, Kiloniellales, Kopriimonadales, Kordiimonadales, Magnetococcales, Parvularculales, Pelagibacterales, Rhizobiales (rhizobiales), Rhodobacterales, Rhodospirillales, Rhodothalassiales, Rickettsiales (rickettsias), Sneathiellales, Sphingomonadales, to class Betaproteobacteria, order Burkholderiales, Ferritrophicales, Ferrovales, Gallionellales, Hydrogenophilales, Methylophilales, Neisseriales, Nitrosomonadales, Procabacteriales, Rhodocyclales, Sulfuricellales, to class Deltaproteobacteria, to class Epsilonproteobacteria, to class Gammaproteobacteria, order Acidiferrobacterales, Acidithiobacillales, Aeromonadales, Alteromonadales, Arenicellales, Cardiobacteriales, Cellvibrionales, Chromatiales, Enterobacteriales, Legionellales, Methylococcales, Oceanospirillales, Orbales, Pasteurellales, Pseudomonadales, Salinisphaerales, Thiotrichales, Vibrionales, Xanthomonadales, to class Oligoflexia, to order Oligoflexales, to class Zetaproteobacteria or to order Mariprofundales.

Among the order Bacillales, the microorganism preferably is of family Alicyclobacillaceae, Bacillaceae, Listeriaceae, Paenibacillaceae, Planococcaceae, Sporolactobacillaceae or Thermoactinomycetaceae. Among the family Alicyclobacillaceae, the microorganism preferably is of any of the genera *Alicyclobacillus*, *Effusibacillus*, *Kyrpidia* or *Tumebacillus*. Among the family Bacillaceae, the microorganism preferably is of any of the genera *Aeribacillus*,

*Alkalibacillus, Allobacillus, Alteribacillus, Amphibacillus, Amylobacillus, Anaerobacillus, Anoxybacillus, Aquibacillus, Aquisalibacillus, Bacillus, Caldalkalibacillus, Caldibacillus, Calditerricola, Cerasibacillus, Domibacillus, Falsibacillus, Fictibacillus, Filobacillus, Geobacillus, Gracilibacillus, Halalkalibacillus, Halobacillus, Halolactibacillus, Hydrogenibacillus, Lentibacillus, Lysinibacillus, Marinococcus, Microaerobacter, Natribacillus, Natronobacillus, Oceanobacillus, Ornithinibacillus, Paraliobacillus, Paucisalibacillus, Piscibacillus, Pontibacillus, Pseudogracilibacillus, Psychrobacillus, Saccharococcus, Salimicrobium, Salinibacillus, Salirhabdus, Salisediminibacterium, Saliterribacillus, Salsuginibacillus, Sediminibacillus, Sinibacillus, Streptohalobacillus, Tenuibacillus, Tepidibacillus, Terribacillus, Texcoconibacillus, Thalassobacillus, Thermolongibacillus, Virgibacillus* or *Vulcanibacillus*. Among the family Listeriaceae, the microorganism preferably is of any of the genera Brochothrix or *Listeria*. Among the family Paenibacillaceae, the microorganism preferably is of any of the genera *Ammoniibacillus, Aneurinibacillus*, (group), *Brevibacillus, Cohnella, Fontibacillus, Gorillibacterium, Paenibacillus, Saccharibacillus* or *Thermobacillus*. Among the family Pasteuriaceae, the microorganism preferably is of genus Pasteuria Among the family Planococcaceae, the microorganism preferably is of any of the genera *Bhargavaea, Caryophanon, Chryseomicrobium, Crocinobacterium, Filibacter, Jeotgalibacillus, Kurthia, Paenisporosarcina, Planococcus, Planomicrobium, Rummeliibacillus, Savagea, Solibacillus, Sporosarcina, Ureibacillus* or *Viridibacillus*. Among the family Sporolactobacillaceae, the microorganism preferably is of any of the genera *Pullulanibacillus, Scopulibacillus, Sinobaca, Sporolactobacillus* or *Tuberibacillus*. Among the family Staphylococcaceae, the microorganism preferably is of any of the genera *Aliicoccus, Jeotgalicoccus, Macrococcus, Nosocomiicoccus, Salinicoccus* or *Staphylococcus*. Among the family Thermoactinomycetaceae, the microorganism preferably is of any of the genera *Desmospora, Geothermomicrobium, Hazenella, Kroppenstedtia, Laceyella, Lihuaxuella, Marininema, Marinithermofilum, Mechercharimyces, Melghirimyces, Novibacillus, Planifilum, Polycladomyces, Salinithrix, Seinonella, Shimazuella, Thermoactinomyces* or *Thermoflavimicrobium*. Among the order Enterobacteriaceae, the microorganism preferably is of family Enterobacteriaceae, and even more preferably of any of the genera *Aranicola, Arsenophonus, Averyella, Biostraticola, Brenneria, Buchnera, Budvicia, Buttiauxella, Cedecea, Citrobacter, Cosenzaea, Cronobacter, Dickeya, Edwardsiella, Enterobacter, Erwinia, Escherichia, Ewingella, Franconibacter, Gibbsiella, Grimontella, Guhaiyinggella, Hafnia, Klebsiella, Kluyvera, Kosakonia, Leclercia, Lelliottia, Leminorella, Lonsdalea, Mangrovibacter, Margalefia, Moellerella, Morganella, Obesumbacterium, Pantoea, Pectobacterium, Phaseolibacter, Photorhabdus, Phytobacter, Plesiomonas, Pluralibacter, Pragia, Proteus, Providencia, Pseudocitrobacter, Rahnella, Raoultella, Rosenbergiella, Rouxiella, Salmonella, Samsonia, Serratia, Shigella, Shimwellia, Siccibacter, Sodalis, Tatumella, Thorsellia, Tiedjeia, Trabulsiella, Wiggleswor-thia, Xenorhabdus, Yersinia* and *Yokenella*. Among the order Pseudomonadales, the microorganism is preferably of family Moraxellaceae, and among these is preferably of any of the genera, *Acinetobacter, Alkanindiges, Enhydrobacter, Faucicola, Moraxella, Paraperlucidibaca, Perlucidibaca* and *Psychrobacter*, or, equally preferred, the microorganism is of family Pseudomonadaceae, and among these preferably is of any of the genera *Azotobacter* (group), *Mesophilobacter, Permianibacter, Pseudomonas, Rugamonas, Serpens* and *Thiopseudomonas*.

Among the order Lactobacillales, the microorganism preferably belongs to any of the families Aerococcaceae, Carnobacteriaceae, Enterococcaceae, Lactobacillaceae, Leuconostocaceae and Streptococcaceae. Among the family Aerococcaceae, the microorganism preferably belongs to any of the genera *Abiotrophia, Aerococcus, Dolosicoccus, Eremococcus, Facklamia, Globicatella* or *Ignavigranum*. Among the family Carnobacteriaceae, the microorganism preferably belongs to any of the genera *Agitococcus, Alkalibacterium, Allofustis, Alloiococcus, Atopobacter, Atopococcus, Atopostipes, Carnobacterium, Desemzia, Dolosigranulum, Granulicatella, Isobaculum, Jeotgalibaca, Lacticigenium, Marinilactibacillus, Pisciglobus* or *Trichococcus*. Among the family Enterococcaceae, the microorganism preferably belongs to any of the genera *Bavariicoccus, Catellicoccus, Enterococcus, Melissococcus, Pilibacter, Tetragenococcus* or *Vagococcus*. Among the family Lactobacillaceae, the microorganism preferably belongs to any of the genera *Lactobacillus, Pediococcus* or *Sharpea*. Among the family Leuconostocaceae, the microorganism preferably belongs to any of the genera *Convivina, Fructobacillus, Leuconostoc, Oenococcus* or *Weissella*. Among the family Streptococcaceae, the microorganism preferably belongs to any of the genera *Lactococcus* (lactic streptococci), *Lactovum, Okadaella* or *Streptococcus*.

Preferably, the microorganism is a *Bacillus* cell, e.g., *Bacillus alkalophius, Bacillus amyloliquefaciens, Bacillus brevis, Bacillus circulans, Bacillus clausii, Bacillus coagulans, Bacillus firmus, Bacillus Jautus, Bacillus lentus, Bacillus licheniformis, Bacillus megaterium, Bacillus pumilus, Bacillus stearothermophilus, Bacillus subtilis*, and *Bacillus thuringiensis*. Most preferred, the prokaryote is a *Bacillus* cell, preferably, a *Bacillus* cell of *Bacillus subtilis, Bacillus pumilus, Bacillus licheniformis*, or *Bacillus lentus*, most preferably, *Bacillus licheniformis*.

The invention also provides a method for producing a catalase, comprising the steps of a) providing a microorganism according to the invention, and b) cultivating the microorganism under conditions allowing for the expression of said gene.

As indicated above, the microorganism of the present invention comprises a catalase gene coding for a catalase polypeptide of the invention. To allow for the expression of said catalase gene, the gene preferably is operably linked to one or more control sequences that direct the production of the gene product, that is the catalase or fragment thereof. Preferred catalases including variants and fragments thereof and corresponding genes have been described above.

Also described above are preferred control sequences. Thus, by using a microorganism of the present invention it is possible to produce a catalase of the present invention having high catalase activity. It is furthermore possible to produce such catalase under conditions specifically selected by the skilled person in accordance with the corresponding control sequence or control sequences.

The catalase can be produced as an intracellular protein or can be secreted from the microorganism. In the first case catalase activity is mostly manifest in the producing microorganism itself. Such microorganism therefore has the advantage of increased tolerance against hydrogen peroxide compared to a microorganism not producing a catalase of the present invention.

The invention correspondingly provides a method for increasing hydrogen peroxide tolerance of a microorganism, comprising
a) providing a microorganism according to the invention in said medium, and
b) cultivating the microorganism under conditions allowing for the expression of said catalase gene.

As indicated above, it is possible to further increase hydrogen peroxide tolerance of said microorganism by exposing the microorganism to a low dose of hydrogen peroxide, wherein the dose is chosen such induce expression of the catalase gene of the present invention under the control of a hydrogen peroxide inducible control sequence. The skilled person will furthermore choose the dose of hydrogen peroxide such that oxidative stress of the microorganism is kept sufficiently low to allow the microorganism to continue producing the catalase. Preferred doses of hydrogen peroxide are 5-10 µM.

The invention also provides a method for removing hydrogen peroxide from a medium, comprising the steps of
a) transforming a microorganism with a recombinant nucleic acid of the invention, or providing a microorganism of the invention, and
b) cultivating the microorganism under conditions allowing for the expression of said gene.

Cultivation under suitable conditions to produce a culture comprising the catalase of the present invention allows to materialise the advantages inherent in the activity of the catalase of the present invention and thus to remove hydrogen peroxide from said medium in which the microorganism is producing said catalase. The microorganism will take up hydrogen peroxide from the medium and have it reduced by the catalase of the present invention produced by said microorganism. The method thus effectively reduces hydrogen peroxide concentration of a medium, preferably of a fermentation medium.

Instead of cultivating the microorganism in the medium, the invention also envisages a method for removing hydrogen peroxide from a medium, comprising the steps of
a) cultivating a microorganism of the present invention in a first medium under conditions allowing for the expression of said catalase, and
b) mix the medium from which hydrogen peroxide is to be removed (second medium) with an cell-free extract of said microorganism grown in step a).

The cell-free extract suitably comprises the catalase of the present invention. This way it is possible to remove hydrogen peroxide from the second medium without having the microorganism of the present invention consume constituents of said second medium. Where the second medium is a fermentation medium, it is particularly preferred that said second medium comprises a production microorganism for producing a substance of interest. This way, the production microorganism can benefit from the action of the catalase of the present invention without having to be co-cultivated with the microorganism of the present invention, and also without having to produce the catalase of the present invention by itself.

The invention also provides a method for protecting a microbially produced substance against oxidation, comprising
a) transforming a microorganism capable of producing said substance with a recombinant nucleic acid according to the invention, or providing a microorganism of the present invention, and
b) cultivating the microorganism under conditions allowing for the expression of said catalase gene.

As indicated above, expression of said catalase gene of the present invention effectively reduces the concentration of hydrogen peroxide within the microorganism and/or in a surrounding medium. Thus, the substance produced by said microorganism essentially benefits from the action of the catalase and is thereby at least partly protected against oxidation. Protein oxidation can be measured by a thiol modification assay indicating oxidation of the thiol groups of the cysteines and subsequent disulfide bond formation by using mass spectrometry (Schroeter R, Voigt B, Jürgen B, Methling K, Pöther D C, Schäfer H, Albrecht D, Mostertz J, Mäder U, Evers S, Maurer K H, Lalk M, Mascher T, Hecker M, Schweder T. The peroxide stress response of *Bacillus licheniformis*. Proteomics. 2011 July; 11(14):2851-66. doi: 10.1002/pmic.201000461). Furthermore, oxidation of cysteines can be specifically determined using the iodoTMT reagents (Thermo Scientific). To have the catalase gene induced once sufficient amounts of the substance have been produced. Such induction allows to protect the substance from oxidation without unnecessarily sacrificing nutrients that could be used for producing said substance.

The invention thus also provides a fermentation method for producing a fermentation product, comprising the steps of
a) providing a microorganism according to the invention, and
b) cultivating the microorganism under conditions allowing for the expression of said catalase gene and also allowing the production of said fermentation product.

As indicated above, expression of said catalase gene of the present invention allows to protect a microbially produced substance against oxidation, thus effectively protecting fermentation products. Protection is conferred as long as the fermentation product is in contact or mixed with an active catalase according to the present invention. Thus, the fermentation method of the present invention provides protection for a fermentation product during fermentation and also during downstream processing. Downstream processing includes cell disruption steps like cell lysis and homogenisation.

As indicated above, the fermentation may be performed by co-cultivating a microorganism producing the fermentation product (production strain) and a microorganism producing the catalase of the present invention. This way it is possible to reduce hydrogen peroxide concentration of a fermentation medium without having to modify the production strain producing said fermentation product.

Thus, in a preferred embodiment, the invention is directed to a fermentation method for producing a fermentation product, comprising the steps of
a) providing a first microorganism comprising the catalase gene according to the invention,
b) providing a second microorganism capable of producing the fermentation product, preferably by comprising a gene encoding for the fermentation product, and
c) cultivating the first and the second microorganism together under conditions allowing for the expression of said catalase gene and also allowing the production of said fermentation product.

In this embodiment, the first microorganism comprising the catalase gene and the second microorganism producing the fermentation product can be of the same or of a different species. Preferably, the first and the second microorganism are of the same species.

More preferably, however, the production strain for producing the fermentation product also expresses the catalase of the present invention. In such cases the production strain is a microorganism of the present invention. This way the catalase is produced in close proximity, that is within the same microorganism also producing the desired fermentation product. Thus, the fermentation product can be thoroughly mixed with the catalase of the present invention in one compartment (that is within the same microorganism or compartment thereof) and thus benefit from the catalase activity without the catalase having to be transported to the fermentation product.

Thus, in a preferred embodiment, the invention is directed to a fermentation method for producing a fermentation product, comprising the steps of
a) providing a microorganism comprising the catalase gene according to the invention and being capable of producing the fermentation product, preferably by comprising a gene encoding the fermentation product, and
b) cultivating the microorganism under conditions allowing for the expression of said catalase gene and also allowing the production of said fermentation product.

The microorganism being capable of producing the fermentation product may comprise the gene encoding the fermentation product or one or more genes encoding the one or more proteins being involved in the production of the fermentation product in its genome or on a plasmid. The microorganism can also comprise said genes on one or more plasmids. The gene encoding the fermentation product or one or more genes encoding the one or more proteins being involved in the production of the fermentation product can be heterologous or homologous genes, preferably heterologous genes.

Preferably, the microorganism being capable of producing the fermentation product comprises said gene encoding the fermentation product or one or more genes encoding the one or more proteins being involved in the production of the fermentation product operably linked to one or more control sequences that direct the production of the gene product. The microorganism can comprise the gene under the control of one or more heterologous or homologous control sequences, preferably heterologous control sequences.

The microorganism producing the fermentation product can be a prokaryote or a eukaryote, preferably a bacteria, an archaea, a fungal cell, a yeast cell or a eukaryotic cell as described above for the catalase expressing microorganism. Useful prokaryotes are bacterial cells such as gram positive or gram negative bacteria. Preferred useful gram positive bacteria include, but are not limited to, a *Bacillus* cell, e.g., *Bacillus alkalophius*, *Bacillus amyloliquefaciens*, *Bacillus brevis*, *Bacillus circulans*, *Bacillus clausii*, *Bacillus coagulans*, *Bacillus firmus*, *Bacillus Jautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis*. Most preferred, the prokaryote is a *Bacillus* cell, preferably, a *Bacillus* cell of *Bacillus subtilis*, *Bacillus pumilus*, *Bacillus licheniformis*, or *Bacillus lentus*, most preferably, *Bacillus licheniformis*.

Where the catalase gene coding for the catalase of the present invention is under the control of one or more control sequences that allow inducible expression of said gene, treating the microorganism with a small dose of the inductor (possibly hydrogen peroxide) allows to selectively increase catalase production at a desired time during fermentation, thereby providing additional protection of the desired fermentation product against oxidation by hydrogen peroxide.

The microbially produced substance (also called "fermentation product") preferably is a protein. The protein can be a homologous or heterologous in view of the producing microorganism. Preferably the substance is an enzyme. The enzyme preferably is selected from the group consisting of protease, amylase, carbohydrase, lipase, cellulase, pullulanase, cutinase, pectinase, mannanase, arabinase, galactanase, xylanase, oxidase, e.g. laccase, peroxidase, isomerase, transferase, kinase, and phosphatase, preferably protease. Preferred proteases are subtilisin proteases. Preferred subtilisin proteases are selected from the group consisting of: subtilisin 168, subtilisin BPN', subtilisin Carlsberg, subtilisin DY, subtilisin 147, subtilisin 309, and variants thereof.

The fermentation broth resulting from the method of the present invention may be further processed by methods known in the art. For example, the fermentation product can be purified or partially purified by one or more downstream methods known in the art, e.g., crystallization, precipitation, microfiltration, centrifugation, ultra-filtration, extraction, decolorization, chromatography, de-odorization, spray-drying, or evaporation.

EXAMPLES

The following Examples are provided in order to demonstrate and further illustrate certain embodiments and aspects of the present invention and are not to be construed as limiting the scope thereof.

Materials and Methods

*Bacillus pumilus* SAFR-032 (Gioia J, Yerrapragada S, Qin X, Jiang H, Igboeli O C, et al. (2007) Paradoxical DNA repair and peroxide resistance gene conservation in *Bacillus pumilus* SAFR-032. PLoS One 2: e928), *Bacillus licheniformis* DSM13 (Waschkau B, Waldeck J, Wieland S, Eichstadt R, Meinhardt F (2008) Generation of readily transformable *Bacillus licheniformis* mutants. Appl Microbiol Biotechnol 78: 181-188) and *Bacillus subtilis* 168 (Burkholder P R, Giles N H, Jr. (1947) Induced biochemical mutations in *Bacillus subtilis*. Am J Bot 34: 345-348) were used in this study. Cells were grown aerobically at 37° C. and 180 rpm in a chemically defined medium containing 15 mM (NH4)2SO4, 8 mM MgSO4×7H2O, 27 mM KCl, 7 mM Na-citrate×2H2O, 50 mM Tris-HCl (pH 7.5) supplemented with 1.8 mM KH2PO4, 2 mM CaCl2), 1 μM FeSO4×7H2O, 10 μM MnSO4×4H2O, 4.5 mM glutamate, 62.4 μM tryptophane 0.2% w/v glucose and 0.04 μM biotin.

Construction of Mutant Strains

The linear DNA fragment carrying the *B. pumilus* katX2 gene, the spectinomycin resistance marker and the homologous flanking sequences of *B. subtilis* was constructed using primers extended by several nucleotides homologous to the connecting upstream/downstream-fragment. A 600 kb upstream-fragment containing the regulatory structures of *B. subtilis* katA was combined with the *B. pumilus* katX2-gene, beginning with the ATG-start-codon and ending with the stop-codon. The spectinomycin resistance gene was fused to a 600 kb downstream fragment beginning right behind the *B. subtilis* katA stop codon. In a second step both fusion products were combined.

Purification, fusing and transformation of the PCR products was carried out according to Reder et al. Mutants were selected on LB agar plates containing 200 μg/mL spectinomycin. For the verification of the knock-out and knock-in mutants, chromosomal DNA amplified and finally sequenced by Eurofins (http://www.eurofinsgenomics.eu/de/home.aspx).

Sample Preparation

Cells were harvested or stressed at an OD500 of 0.6 with various concentrations of H2O2. Samples used for 2D-PAGE analyses, fluorescence thiol modification assays and the quantification of catalase protein accumulation were stressed with 50 µM (*B. subtilis, B. subtilis* katA::katX2, *B. licheniformis*) and 2 mM (*B. pumilus*) H2O2, respectively. Samples used for the catalase activity assay were stressed using one-tenth of these concentrations.

Cells were harvested by centrifugation (20 000×g, 4° C., 10 min) followed by two washing steps with 100 mM Tris-HCl buffer, pH 7.5. Cell disruption was done by sonication after resuspension in TE buffer (10 mM Tris, pH 7.5, 10 mM EDTA) containing 1.4 mM PMSF. For absolute protein quantification an in-solution digestion of proteins with TE buffer without PMSF was used. Protein concentration was determined with RotiNanoquant (Roth).

2D-PAGE, gel imaging, relative quantification and protein identification 200 µg protein were adjusted to 306 µL with 2 M thiourea/8 M Urea, mixed with 34 µL CHAPS solution (20 mM DTT, 1% w/v CHAPS, 0.5% v/v Pharmalyte, pH 4-7 or 3-10) and loaded onto commercially available IPG strips (SERVA Electrophoresis) in the pH-range of 4-7. IEF was performed according to Buttner et al. (Buttner K, Bernhardt J, Scharf C, Schmid R, Mader U, et al. (2001) A comprehensive two-dimensional map of cytosolic proteins of *Bacillus subtilis*. Electrophoresis 22: 2908-2935). Equilibration of the strips containing the focused proteins was performed in solutions containing DTT and iodacetamide, respectively, as described by Gorg et al. (Gorg A, Boguth G, Obermaier C, Posch A, Weiss W (1995) Two-dimensional polyacrylamide gel electrophoresis with immobilized pH gradients in the first dimension (IPG-Dalt): the state of the art and the controversy of vertical versus horizontal systems. Electrophoresis 16: 1079-1086). Gels of 12.5% acrylamide and 2.6% bisacrylamide were used for separation in the second dimension. Gels were stained with Flamingo Fluorescent Gel Stain (Bio-Rad Laboratories) according to the manufacturer instructions.

Analysis of the gel images and spot quantification was performed as described by Wolf et al. using the Delta2D software version 4.4 (Decodon) Wolf C, Hochgräfe F, Kusch H, Albrecht D, Hecker M, et al. (2008) Proteomic analysis of antioxidant strategies of *Staphylococcus aureus: diverse responses to different oxidants. Proteomics* 8: 3139-3153). Protein spots were excised from the gels (Ettan Spot Picker, GE Healthcare), digested and spotted onto MALDI targets (Ettan Spot Handling Workstation, GE Healthcare). MS-Analysis of the targets was performed by MALDI-TOF-MS/MS using the Proteome Analyzer 4800 (Applied Biosystems) and peak lists were searched with MASCOT search engine version 2.1.0.4 (Matrix Science) and search parameters as described by Wolf et al. (Wolf C, Hochgräfe F, Kusch H, Albrecht D, Hecker M, et al. (2008) Proteomic analysis of antioxidant strategies of *Staphylococcus aureus*: diverse responses to different oxidants. Proteomics 8: 3139-3153).

Label-Free Quantification (LC-IMSE)

In-solution digestion of protein extracts with trypsin was done according to the method described previously (Muntel J, Fromion V, Goelzer A, Maabeta S, Mader U, et al. (2014) Comprehensive absolute quantification of the cytosolic proteome of *Bacillus subtilis* by data independent, parallel fragmentation in liquid chromatography/mass spectrometry (LC/MS(E)). Mol Cell Proteomics 13: 1008-1019). Desalting of peptides prior to mass spectrometry analysis using stage tips was achieved using a standard protocol (Rappsilber J, Mann M, Ishihama Y (2007) Protocol for micropurification, enrichment, pre-fractionation and storage of peptides for proteomics using StageTips. Nat Protoc 2: 1896-1906). For absolute quantification the peptide mix was spiked with a tryptic digest of yeast alcohol dehydrogenase (Waters) at a final concentration of 50 fmol/µL.

The nanoACQUITY™ UPLC™ system (Waters) was used to separate the peptide mixture and to introduce the samples into the mass spectrometer. The peptide mixture was directly loaded on an analytical column (nanoACQUITY™ UPLC™ column, BEH300 C18, 1.7 mm, 75 mm_200 mm, Waters). Separation of peptides for IMSE (MSE with ion mobility separation) was done with a 90 min gradient from 5% buffer B to 40% buffer B. All MSE analyses were performed as previously described (Muntel J, Fromion V, Goelzer A, Maabeta S, Mader U, et al. (2014) Comprehensive absolute quantification of the cytosolic proteome of *Bacillus subtilis* by data independent, parallel fragmentation in liquid chromatography/mass spectrometry (LC/MS(E)). Mol Cell Proteomics 13: 1008-1019). The only modification was, that the collision energy was alternated between 4 eV in the precursor ion trace and a ramp 25-45 eV for fragment ion trace. Wave velocity was ramped from 1,000-400 m/s, wave height was set to 40 V.

LC-IMSE data were processed using PLGS v3.0.1. Processing parameter were set as follows: Chromatographic peak width and MS TOF resolution were set to automatic, lock mass charge 2 set to 785.8426 Da/e with a lock mass window of 0.25 Da, low energy threshold 200.0 counts, elevated energy threshold 20.0 counts, intensity threshold 750 counts. The data were searched against a randomized *Bacillus subtilis* 168 database (NCBI, version August 2014) with added amino acid sequence of *B. pumilus* SAFR032 KatX protein, laboratory contaminants and yeast ADH1 sequence (8,438 entries). For positive protein identification the following criteria had to be met: 1 fragment ion matched per peptide, 5 fragment ions matched per protein, 1 peptide matched per protein; 2 missed cleavages allowed, primary digest reagent: trypsin, fixed modification: carbamidomethylation C (+57.0215), variable modifications: deamidation N, Q (+0.9840), oxidation M (+15.9949), pyrrolidonecarboxylacid N-TERM (−27.9949). The protein false discovery rate (FDR) was set to 5%. For the final analysis only 2 peptide identifications were considered. A protein had to be identified in at least two out of 3 technical replicates per time point; this took the FDR on protein level to less than 3%. 3 biological replicates for each time point were analyzed.

Data generated by the IMSE mode were corrected for detector saturation effects by implementing a correction factor based on the ion accounting output files that were created for each sample by the PLGS software. The correction factor (cf) was calculated using following equation.

$$\Sigma Ipeptide/\Sigma Iproduct * 1/m = cf$$

Where ΣIpeptide and ΣIproduct are the matched peptide/product intensity sums, m is the median of the ratios ΣIpeptide/ΣIproduct calculated for every protein quantified in a sample.

Catalase Activity Assay

Cells were grown to an OD500 nm of 0.6. Right before starting the assay, a working solution of 25 µg/mL lactoperoxidase and 0.5 M dicarboxidine dihydrochloride (both Sigma-Aldrich) was prepared. A final concentration of 2 mM hydrogen peroxide was added to the cell cultures. To measure the H2O2 concentration remaining in the culture at certain time points, 25 µL of the culture was mixed with 500 µL working solution and absorbance at 450 nm was measured as described (Ma Q, Wood T K (2011) Protein acetylation in prokaryotes increases stress resistance. Biochem Biophys Res Commun 410: 846-851).

The same protocol was used to determine the degradation of H2O2 by cytosolic protein extracts. 5 µg of protein extract were filled up with catalase assay buffer (Catalase Assay Kit, BioVision) to 200 µL. H2O2 was added to a final concentration of 2 mM and the extracts were incubated at 30° C. The remaining H2O2 concentration was measured as described above at defined time points.

Fluorescence Thiol Modification Assay and Analysis of Protein Modifications

Proteins with reversibly oxidized cysteines were visualized using a protocol described by Hochgräfe et al. (Hochgräfe F, Mostertz J, Albrecht D, Hecker M (2005) Fluorescence thiol modification assay: oxidatively modified proteins in Bacillus subtilis. Mol Microbiol 58: 409-425). Protein extracts were purified and pre-stained as described and loaded onto IPG-strips in the pH-range 4-7 (SERVA Electrophoresis). 2D-PAGE was performed as described above in the dark. Following fluorescence scanning of reversibly oxidized proteins the gels were stained with Flamingo Fluorescent Gel Stain (Bio-Rad Laboratories). Spot quantification and MS-analyses were performed as described above.

For the analysis of possible modifications protein spots were excised from the gels as described above, destained (0.2 M NH4HCO3, 30% acetonitrile) and double digested with trypsin and chymotrypsin (both Promega). Peptide extraction was performed by covering the gel pieces with ultra-pure water (prepared with a Sartorius Stedim unit) and 15 min incubation in an ultrasonic water bath. Peptides were detected by LC-MS/MS using an Orbitrap Elite (Thermo Fisher Scientific). Database searches were conducted with the SEQUEST software v28 (rev.12, Thermo Fisher Scientific) against B. subtilis 168 and B. pumilus SAFR-032 database. Data were analyzed using Scaffold proteome viewer version 4.0.5.

Example 1

Figure 2:
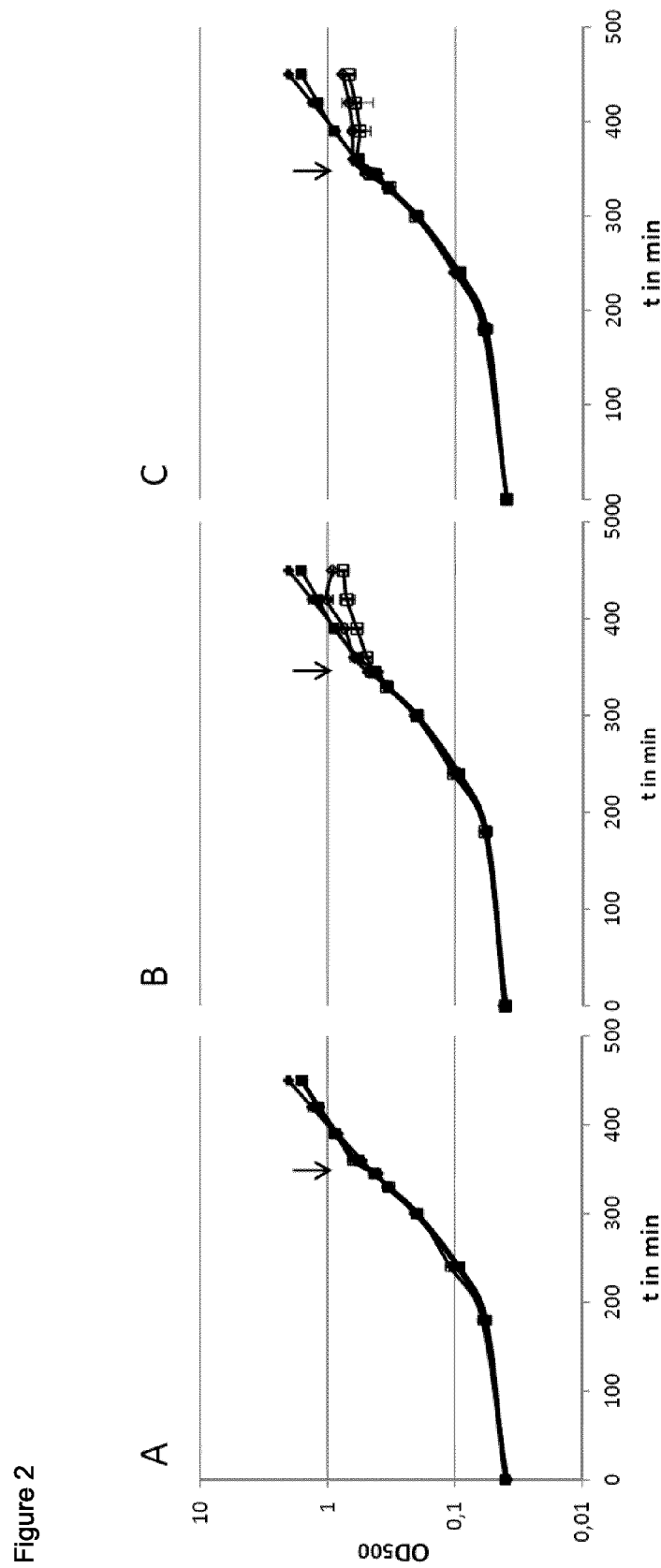
FIG. 2 shows growth curves of *Bacillus* cultures under different oxidation stress conditions. Depicted are growth curves of *B. subtilis* katX2 mutant (diamonds) compared to *B. subtilis* 168 strain (squares). Control conditions are shown with filled, stressed cultures with empty symbols. Time points of adding the H2O2 are shown by arrows and H2O2 concentrations used were 50 µM (A), 200 µM (B) and 2 mM (C).

There was no difference in the growth behavior of the B. subtilis katA::katX2 mutant compared to the wild type strain under control conditions. After the treatment of the wild type strain and the B. subtilis katA::katX2 mutant with 50 µM H2O2 also only a small impact on the growth of both strains could be detected (FIG. 2A). In contrast, the mutant strain showed a significantly lower impact on the growth rate than the wild type when the cells were treated with 200 µM H2O2 (FIG. 2B). Mutant cells continued growth up to an optical density of about 1 whereas the wild type reached a final OD of about 0.75. Increasing the hydrogen peroxide concentration up to 2 mM, a concentration which B. pumilus can withstand, resulted in a nearly complete stop of growth in both B. subtilis strains (FIG. 2C).

The survival of the B. subtilis 168 strain and the katA::katX2 mutant was analyzed using 500 µM H2O2. 23% of the wild type cells survived three minutes after peroxide treatment. At the same time point about 50% of the katA::katX2 mutant cells were still alive. 15 min after addition of H2O2 32% of the katX2-expressing cells were alive whereas only 18% of the wild type cells survived at this time point. These data indicate a 1.5-2-fold higher survivability of the katX2-expressing cells under this oxidative stress conditions.

Example 2

Under control conditions, in all extracts tested the relative spot volume of the vegetative catalase KatA respectively KatX2 was about 0.4-0.5%. The KatX2 spot volume only increased about 1.4-fold in B. pumilus cells 20 min after H2O2 treatment. In B. subtilis cells we detected a 3-fold increase from 0.39% to 1.23% in the amount of KatA after H2O2 treatment indicating that a higher amount of enzyme was present compared to B. pumilus cells. A similar about three-fold increase after addition of H2O2 was also observed for the KatX2 spot in the B. subtilis katA::katX2 mutant.

To gain information on the absolute concentrations of the catalases in the cytoplasm, the gel- and label-free quantification approach LC-IMSE was conducted. The results of this experiment revealed a concentration of KatA of 0.0165 fmol/ng protein extract in exponentially growing B. subtilis cells. KatA accumulation increased up to 0.11 fmol per ng protein extract in hydrogen peroxide stressed cells. In B. pumilus we measured an amount of 0.0385 fmol KatX2 per ng protein extract. 20 min after addition of H2O2, catalase accumulation increased up to about 0.1 fmol per ng cell extract in B. pumilus cells. Based on the lower basal accumulation the induction rate following H2O2 treatment was significantly higher in B. subtilis cells.

Exponentially growing B. subtilis katA::katX2 mutant cells contained 0.026 fmol KatX2 catalase per ng protein extract. Following hydrogen peroxide treatment the KatX2 accumulation increased up to about 0.14 fmol per ng cell extract and therefore it was higher than the KatX2 accumulation in H2O2 stressed B. pumilus cells.

Example 3

Figure 3:
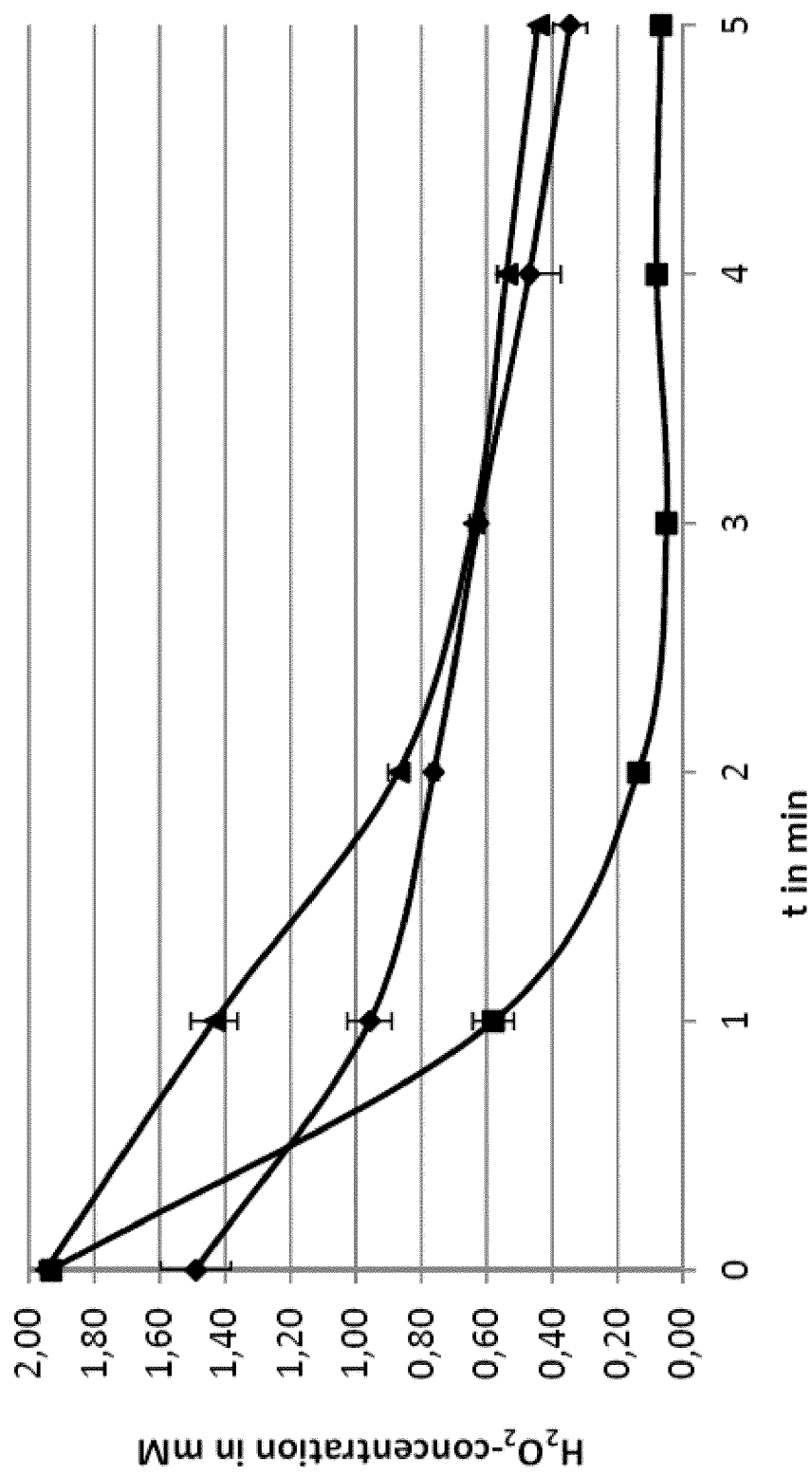
FIG. 3 shows the decrease of H2O2 concentration after adding to the medium of growing cells. Values for *B. subtilis* are shown with diamonds, for *B. licheniformis* with triangles and those for *B. pumilus* are shown with squares.

To analyze how the cells deal with hydrogen peroxide, 2 mM H2O2 were added to growing cells at an OD500 of 0.6. In B. pumilus cultures a significantly faster decrease of hydrogen peroxide concentration was observed than in B. subtilis or B. licheniformis cultures (FIG. 3). After two minutes less than 10% of the added H2O2 was left in the culture. Three minutes after addition, H2O2 was nearly completely disappeared. At the same time, there was about one-third of the initial H2O2 concentration left in the B. subtilis and B. licheniformis cultures.

Figure 4:
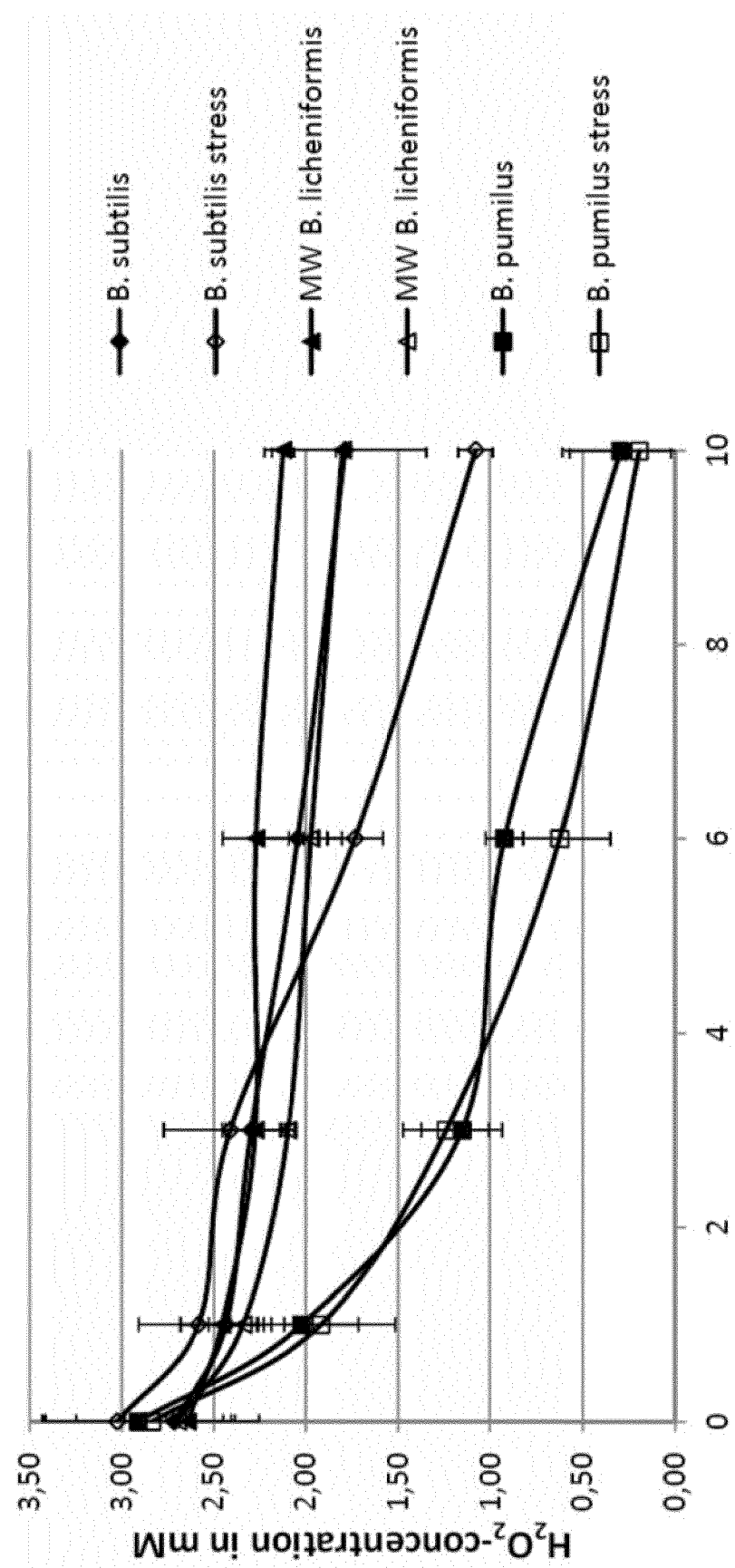
FIG. 4 shows the degradation of H2O2 by cell extracts from *B. subtilis* 168 strain (diamonds), *B. licheniformis* DSM 13 (triangles) and *B. pumilus* SAFR-032 (squares). Extracts from exponentially growing cells are shown with filled symbols, extracts from cells previously stressed are shown with empty symbols.

In a second approach cell extracts were used containing equal amounts of protein to analyze the degradation of H2O2 by the catalases. For this extracts were prepared from exponentially growing cells as well as from cells previously stressed by low amounts of H2O2 (5 µM for B. subtilis and B. licheniformis, 200 µM for B. pumilus) (FIG. 4). As shown in FIG. 4, the added H2O2 concentration was reduced faster in pre-stressed extracts. In both cases, the B. pumilus cell extract degraded the hydrogen peroxide faster than the extracts from the two other organisms. B. subtilis and B. licheniformis protein extracts degraded only about 50% of the added H2O2 within 10 minutes, whereas 80-90% of it was degraded by the B. pumilus extracts.

Figure 5:
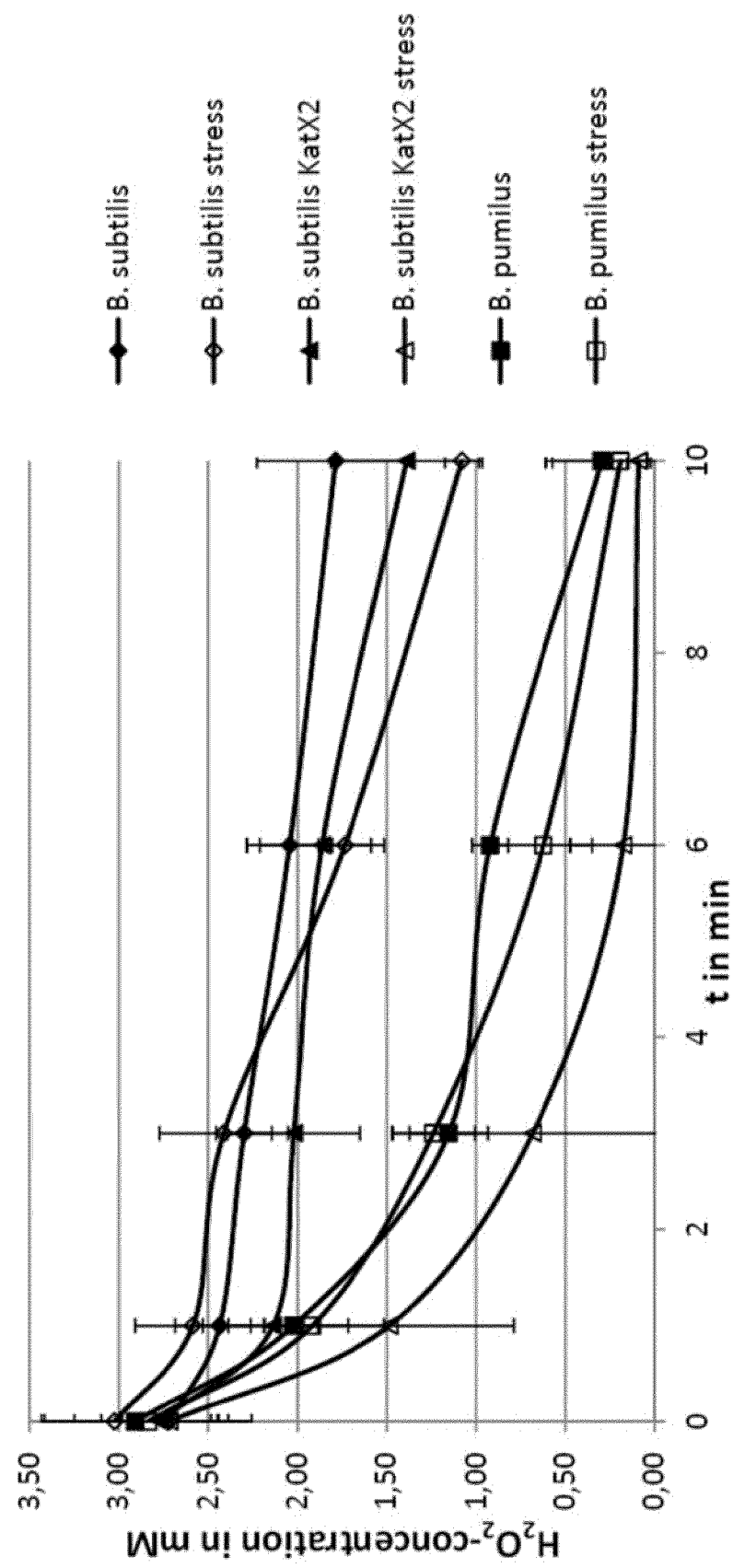
FIG. 5 shows the degradation of H2O2 by cell extracts from *B. subtilis* 168 strain (diamonds), *B. subtilis* katX2 mutant (triangles) and *B. pumilus* SAFR-032 (squares). Extracts from exponentially growing cells are shown with filled symbols, extracts from cells previously stressed are shown with empty symbols.

The degradation rate of extracts from exponentially growing unstressed B. subtilis katA::katX2 mutant cells was comparable to those shown by the wild type. Pre-stressed extracts of the mutant cells degraded the added H2O2 much faster than the corresponding extracts from the other strains and organisms, even faster than the pre-stressed B. pumilus cell extracts (FIG. 5). The higher induction rate of the recombinant catalase KatX2 in B. subtilis following hydrogen peroxide treatment compared to the induction rate observed in stressed B. pumilus resulted in a higher amount of the catalase in the cells.

Example 4

Reversible thiol-modifications in the B. pumilus KatX2 protein was analysed as described above. This procedure uses two different staining methods, one for protein accumulation and one for reversible thiol oxidations. Quantification of proteins is done using relative spot volumes (volume of a spot compared to the volumes of all spots visible on the 2D-gel). The ratio between the spot volumes of a protein spot in the thiol modification staining and the protein accumulation staining is an indicator for the amount of reversible oxidations of the cysteine residues in a protein. In exponentially growing cells, KatX2 cysteine residues were nearly completely reduced. A hydrogen peroxide treatment caused a significant increase of reversible cysteine oxidation. The ratio of thiol modification to protein accumulation increased from about 0.5 to 1.36.

Furthermore, LC-MS/MS analysis was performed to show irreversible oxidation of cysteine residues in the different catalase spots excised from the 2D-gels. This irreversible oxidation cannot be accessed by the fluorescence thiol modification assay. Mass shifts of +32 and +48 were detected in KatX2 expressed by the *B. subtilis* katA:: katX2 mutant representing sulfinic (+32) and sulfonic (+48) acid formation. In *B. pumilus* only formation of a sulfonic acid in the KatX2 cysteine 461 was detected.

The invention claimed is:

1. A method for protecting a microbially produced substance against oxidation, comprising
   a) providing a microorganism capable of producing said substance, the microorganism comprising, as a heterologous gene, a catalase gene encoding
      i) a catalase having at least 90% amino acid sequence identity to SEQ ID NO: 1, or
      ii) a fragment of the catalase according to i), wherein the fragment has catalase activity, and
   b) cultivating the microorganism under conditions such that said catalase gene is expressed and said substance is produced,
   wherein the microbially produced substance is an enzyme selected from the group consisting of protease, amylase, carbohydrase, lipase, cellulase, pullulanase, cutinase, pectinase, mannanase, arabinase, galactanase, xylanase, oxidase, peroxidase, isomerase, kinase, and phosphatase.

2. A fermentation method for producing a fermentation product, comprising the steps of
   a) providing a microorganism capable of producing said fermentation product, the microorganism comprising, as a heterologous gene, a catalase gene encoding
      i) a catalase having at least 90% amino acid sequence identity to SEQ ID NO: 1, or ii) a fragment of the catalase according to i), wherein the fragment has catalase activity, and b) cultivating the microorganism under conditions such that said catalase gene is expressed and said fermentation product is produced, wherein the fermentation product is an enzyme selected from the group consisting of protease, amylase, carbohydrase, lipase, cellulase, pullulanase, cutinase, pectinase, mannanase, arabinase, galactanase, xylanase, oxidase, peroxidase, isomerase, kinase, and phosphatase.

3. The method according to claim 1, wherein the catalase gene is operably linked to a control sequence and the control sequence is or comprises an inducible promotor.

4. The method according to claim 3, wherein the inducible promoter is a hydrogen peroxide inducible promoter.

5. The method according to claim 1, wherein the enzyme is a subtilisin protease.

6. The method according to claim 2, wherein the enzyme is a subtilisin protease.

7. The method according to claim 2, wherein the catalase gene is operably linked to a control sequence and the control sequence is or comprises an inducible promotor.

8. The method according to claim 7, wherein the inducible promoter is a hydrogen peroxide inducible promoter.

9. The method according to claim 1, wherein the catalase gene encodes a catalase having at least 95% amino acid sequence identity to SEQ ID NO: 1 or a fragment thereof having catalase activity.

10. The method according to claim 2, wherein the catalase gene encodes a catalase having at least 95% amino acid sequence identity to SEQ ID NO: 1 or a fragment thereof having catalase activity.

\* \* \* \* \*